(12) United States Patent
Epstein et al.

(10) Patent No.: US 8,478,611 B2
(45) Date of Patent: *Jul. 2, 2013

(54) SYSTEM AND METHOD FOR CLINICAL STRATEGY FOR THERAPEUTIC PHARMACIES

(75) Inventors: Robert S. Epstein, Upper Grandview, NY (US); Tej Anand, Chappaqua, NY (US); Roger Anderson, Lewisville, TX (US); Kenneth Klepper, Franklin Lakes, NJ (US); Mark Proulx, Sparta, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 30 days.

This patent is subject to a terminal disclaimer.

(21) Appl. No.: 12/773,567

(22) Filed: May 4, 2010

(65) Prior Publication Data
US 2010/0217626 A1    Aug. 26, 2010

Related U.S. Application Data

(63) Continuation of application No. 11/542,898, filed on Oct. 4, 2006, now Pat. No. 7,711,583.

(60) Provisional application No. 60/723,581, filed on Oct. 5, 2005.

(51) Int. Cl.
*A61B 5/00* (2006.01)
*G06F 19/00* (2006.01)

(52) U.S. Cl.
USPC .......................................................... 705/3

(58) Field of Classification Search
USPC ....................................................... 705/2, 3
See application file for complete search history.

(56) References Cited

U.S. PATENT DOCUMENTS

| | | | |
|---|---|---|---|
| 5,845,255 A * | 12/1998 | Mayaud | 705/3 |
| 7,711,583 B2 | 5/2010 | Epstein et al. | |
| 2002/0111828 A1 | 8/2002 | Bloder et al. | |
| 2002/0111832 A1* | 8/2002 | Judge | 705/3 |
| 2003/0130873 A1* | 7/2003 | Nevin et al. | 705/3 |
| 2003/0149599 A1* | 8/2003 | Goodall et al. | 705/2 |
| 2003/0167189 A1* | 9/2003 | Lutgen et al. | 705/3 |
| 2003/0225595 A1* | 12/2003 | Helmus et al. | 705/2 |
| 2005/0106205 A1* | 5/2005 | Gillis et al. | 424/423 |
| 2005/0159985 A1* | 7/2005 | Bertram | 705/3 |
| 2006/0089856 A1 | 4/2006 | Kadhiresan et al. | |
| 2006/0149587 A1 | 7/2006 | Hill et al. | |
| 2007/0059685 A1* | 3/2007 | Kohne | 435/5 |
| 2007/0162295 A1* | 7/2007 | Akhtar et al. | 705/1 |

* cited by examiner

*Primary Examiner* — Gerald J. O'Connor
*Assistant Examiner* — Trang Nguyen
(74) *Attorney, Agent, or Firm* — Husch Blackwell LLP

(57) ABSTRACT

A system and method of distributing pharmaceutical prescriptions within a network of pharmacies based on the review of prescription claim data and patient medical state to enable stratification of patients, wherein each pharmacy within the network has been established to handle one or more particular patient medical states.

19 Claims, 23 Drawing Sheets

Prescriber screen
Pharmacy routing

Route overview
Dimensions of routing

If
- Client: --Select--
- Drug: --Select--
- Patient: --Select--
- Index: Clinical appropriateness
- Score: less than 85%
- Order: --Select--
- Regulation: --Select--
- Task: --Select-- then route
- Skill set: --Select--
- Proficiency: --Select--
- Location: Tampa, Florida
- People: Work@Home
- Contact: --Select--
- Task: --Select--

Submit & review

FIG.17

Prescriber screen

Pharmacy routing

Address: http://mcfl1u0b.medco.com:20000/html/clinical_phase2/contact/physician.html

Prescriber: John Miller MD

| | | |
|---|---|---|
| DEA #: | ME123456 | Address: | EA Medical Associates |
| Specialty: | Endocrinology | | 123 Main Street |
| Phone number: | (212)555-1212 | | Florida, NY 10000 |
| Fax number: | (212)555-1213 | Email: | abc@xyz.com |
| Local time: | 12:25 PM | Contact agent: | Nicole Smith, CFNP |
| | (in office) | | Contact history |
| | | Last contact: | xx/xx/2005 |
| | | COE: | Complex |

Channel performance
Phone: 70%
Fax: 5%
Switch rate: 10%
details

Office hours: (call between 12 PM – 3 PM)

| Sun | Mon | Tue | Wed | Thu | Fri | Sat |
|---|---|---|---|---|---|---|
| Closed | 1PM–7PM | 8AM–8PM | Closed | 8AM–8PM | 8AM–5PM | 11AM–5PM |

Open issues

Schedule contact
Resolution history

| Patients Order number Plan sponsor | Protocol/description (legend) | Drug and potency | Correspond-ence | Received date | Targeted delivery date |
|---|---|---|---|---|---|
| Chris Bell (order# 123456545) Plan Sponsor: Client ABC | ▮▮▮ URPDA POS DUR–DRUG ALLERGY | Celebrex 100mg | Qty. 90 Rx# 123456789002 | | | xx/xx/2005 |
| | ▮▮▮ DR–DIS DRUG–DISEASE INTERACTION 428.0 | Celebrex 100mg | Qty. 90 Rx# 123456789002 | | xx/xx/2005 | xx/xx/2005 |
| | ▮▮▮ PPPOT PERSISTENCY OF THERAPY | Digoxin 0.25mg | Qty. 90 Rx# 123456789001 | | xx/xx/2005 | xx/xx/2005 |

FIG.19

Prescriber screen
Pharmacy routing

Prescriber
Patient: Chris Bell (DOB: 01/05/1969 Age: 36 Gender: Male)

| | | | |
|---|---|---|---|
| Phone number: | (201) 555-1111 | COE: | Complex |
| Address: | 123 Main Street Mahwah, NJ 07411 | Known conditions: | -none- |
| | | Known Allergies: | Sulfa |
| Work phone: | (845) 555-1111 | Wellness category: | Complex |
| Work address: | 123 Main Street Ho-Ho-Kus, NJ 07413 | Order status  Patient profile | Medical history |

| | |
|---|---|
| Plan sponsor: | Client ABC |
| Clinical appropriateness: | 82 |
| Financial opportunities (client): | $2060 |
| Financial opputunities (member): | $500 |

| | | Pharmacist: | Michael Adams |
|---|---|---|---|
| | | Date: | 01/05/2005 |
| | | Prescriber: | John Miller MD |
| | | Phone number: | (212)555-1212 |
| | | fax number: | (212)555-1213 |
| | | Local time: | 10:25 AM (in office) |
| | | Address: | EA Medical Associates 123 Main Street Florida, NY 10000 |

Open issues

| Protocol/description (legend) | Drug and potency | Received date | Targeted delivery date | Information | |
|---|---|---|---|---|---|
| ■ URPDA POS DUR-DRUG ALLERGY | Celebrex 100mg 1 Qty. 90 Rx# 123456789002 view Rx image | xx/xx/2005 | xx/xx/2005 | Patient profile indicates allergy to sulfa drugs. details | resolve / call script |
| ■ DR-DIS DRUG-DISEASE INTERACTION 428.0 | Celebrex 100mg 1 Qty. 90 Rx# 123456789002 view Rx image | xx/xx/2005 | xx/xx/2005 | Benefit is limited to situations where the use of other NSAIDs is not warranted. details | resolve / call script |

Clinical - Microsoft Internet Explorer provided by MEDCO HEALTH

File  Edit  View  Favorites  Tools  Help

Back  Forward  Stop  Refresh  Home  Search  Favorites  Media  History  Mail  Print  Edit  Discuss  Control Pad Real.com Address: http://mcf1u0b.medco.com:20000/html/clinical_phase2/contact/dur.html?Next4=resolve    Go  Links

Patient: Chris Bell (DOB: 01/05/1969 Age: 36 Gender: Male)

| | | | |
|---|---|---|---|
| Phone number: | (201) 555-1111 | COE: | Complex |
| Address: | 123 Main Street | Known conditions: | --none-- |
| | Mahwah, NJ 07411 | Known Allergies: | Sulfa |
| Work phone: | (845) 555-1111 | Wellness category: | Complex |
| Work address: | 123 Main Street | | |
| | Ho-Ho-Kus, NJ 07413 | | |

Order status  Patient profile  Medical history

| | | | |
|---|---|---|---|
| Pharmacist: | Michael Adams | | |
| Date: | 01/05/2005 | | |
| Prescriber: | John Miller MD | | |
| Phone number: | (212) 555-1212 | | |
| Fax number: | (212) 555-1213 | | |
| Local time: | 10:25 AM (in office) | | |
| Address: | EA Medical Associates | | |
| | 123 Main Street | | |
| | Florida, NY 10000 | | |

View contact history  Contact notes

| Drug | Strength | Dosage | Directions |
|---|---|---|---|
| Celebrex  Qty. 90 | 100mg | 1x daily | • If a dose is missed, take it as soon as possible. If several hours have passed or it is nearing time for next dose, do not double the dose to catch up, unless advised to do so by your doctor. If more than one dose is missed or it is necessary to establish a new dosage schedule, contact your doctor or pharmacist.<br>• Do not take any over-the-counter or prescription medications or dietary supplements unless advised to do so by your doctor. |
| Rx# 123456789002 | | | |
| RPHRP PENDED REFILL-CXL: S601 | | | |
| RPHAP RPH APPROVED; PROF JUDGEMENT | | | |
| RPHCN RPH CANCELED; S001 | | | |
| RPHFP RPH APPROVED; FALSE POSITIVE | | | |
| RPHAO RPH APPROVED; ORDER NEVER RECV | | | |
| RPHGB RPH APP'D; GENERIC TO BRAND | | | |
| RPHAV RPH APPROVED; VACATION | | | |
| DUPFX DUPLICATE FX FROM MD; CXL S999 | | | |
| RPHCX RPH CANCELLED; NO SOBA | | | |
| RPHAL RPH APPROVED; LOST MEDS | | | |
| TECCN TECH CANCELED; S095 | | | |
| RPHRP PENDED REFILL: CXL S601 | | | | submit

FIG. 22

| Protocol/description (legend) | Drug and potency | Received date | Targeted delivery date | Information | |
|---|---|---|---|---|---|
| ▮ ELPAR PRIOR AUTH REQ'D; ELIGIBILITY | Celebrex 100mg \|Qty. 90 Rx# 123456789002 view Rx image | xx/xx/2005 | xx/xx/2005 | Benefit is limited to situations where the use of other NSAIDs is not warranted. details | resolve call script |
| ▮ PPPOT PERSISTENCY OF THERAPY | Digoxin 0.25mg \|Qty.90 Rx# 123456789001 view Rx image | xx/xx/2005 | xx/xx/2005 | Gap in therapy exceeds 60 days. details | resolve call script |
| ▯ DRG34 GENERIC NOW AVAIL; ACCEL SUBST | Prevacid 30mg \|Qty. 30 Rx# 123456789003 view Rx image | xx/xx/2005 | xx/xx/2005 | Omeprazole is a generic alternative to Prevacid. details | resolve call script |
| ▯ PPCDO MGD CARE DOSE OPTIMIZATION | Amaryl 1mg \|Qty. 180 Rx# 123456789003 view Rx image | xx/xx/2005 | xx/xx/2005 | Benefit for a quantity greater than 1 dosage unit per day is limited to situations where 1 dosage unit per day has caused intolerant side effects. details | resolve call script |
| ▯ URPER POS DUR-REF TOO SOON | Amaryl 1mg \|Qty.180 Rx# 123456789003 view Rx image | xx/xx/2005 | xx/xx/2005 | Refill occurs before days supply of previous filling should have been exhausted. details | resolve call script |
| Resolved issues | | | | | |
| Protocol/description (legend) | Drug and potency | Received date | Targeted delivery date | Information | |
| ▮ URPDA POS DUR-DRUG ALLERGY | Celebrex 100mg \|Qty.90 Rx# 123456789002 view Rx image | xx/xx/2005 | xx/xx/2005 | Patient profile indicates allergy to sulfa drugs. details | resolved |

Legend: ▮ !URGENT  ▮ High importance  ▯ Medium importance  — Low importance

SYSTEM AND METHOD FOR CLINICAL STRATEGY FOR THERAPEUTIC PHARMACIES

CROSS REFERENCE TO RELATED APPLICATION

This application is a continuation patent application of U.S. patent application Ser. No. 11/542,898, filed on Oct. 4, 2006, and issued on May 4, 2010, as U.S. Pat. No. 7,711,583, which claims the benefit under 35 U.S.C. §119(e) of U.S. Patent Application No. 60/723,581, filed Oct. 4, 2005, each of which is hereby incorporated by reference herein in its entirety.

FIELD OF THE INVENTION

The present invention relates to a system and method for computer analysis of a patient's medical records and prescription claims, suitable for stratifying the patient into therapeutic and wellness categories, wherein patient prescriptions may be routed to therapeutic pharmacies particularly established to resolve protocols and fill prescriptions based upon patient therapeutic and wellness categories. The invention relates to a system and method for integrating therapeutic and wellness categories with clinical scores to better manage prescription benefit services. Further, the invention relates to a system and method for routing and filling prescriptions in a therapeutic pharmacy network to optimally balance prescription filling workloads.

BACKGROUND OF THE INVENTION

Heretofore, pharmaceutical dispensing, the business of dispensing a pharmaceutical medication based upon a doctor's prescription, e.g., general retail pharmacy sites, have been structured as stand-alone operations, wherein an individual pharmacy had the capacity to fill and dispense any number of medications to a patient. A pharmacist within the retail pharmacy has the general knowledge and experience to resolve a number of discrepancies in the prescription, determine if the patient had appropriate insurance coverage, and, as necessary, formulate and dispense the prescribed medication. The trend in retail pharmaceutical operations had been to establish many identical drug stores within a network of pharmacies, so that each pharmacy within the network virtually mirror imaged all the other stores within the chain. Each pharmacy within the established chain of pharmacies is stocked with identical prescriptive medications, over-the-counter and retail products, and staffed by licensed pharmacists capable of dispensing all FDA-approved medications. Such a network of pharmacies had an advantage to the operator thereof in retail establishments dispersed throughout a geographical region, wherein a patient would bring a prescription to the pharmacy counter of the local drug store and wait for a medication recently prescribed by her doctor to be dispensed. However, with the advent of today's mail order pharmaceutical services, wherein a prescription may be transmitted to the pharmacy via electronic communications, e.g., telephone, the Internet, facsimile, etc., to a call-in center, dispatched to a pharmacy within a network for filling, and mailed to the patient, many of the considerations associated with a 'neighborhood pharmacy' become less important. The neighborhood pharmacy's concern with stocking a large variety of drugs to meet patients' needs and delivering prescriptions to waiting patients are no longer of paramount consideration. Other factors that will make a mail order network of pharmacies more efficient and economic need to be considered.

SUMMARY OF THE INVENTION

The present invention relates to a system and method for computer implemented analysis of patient medical records and/or prescription claims to provide patient stratifications, therapeutic conditions and clinical score information, wherein the information is suitable for routing prescriptions to specialized therapeutic pharmacies within a network of pharmacies for improving pharmaceutical services. More particularly the invention relates to a method for routing a pharmaceutical prescription to a therapeutic pharmacy within a network of therapeutic pharmacies, wherein the method is suitable for selecting a therapeutic pharmacy for filling the prescription based upon patient medical records and prescription claims, comprising the steps of:

a. means for receiving a pharmaceutical prescription for a patient at a pharmacy intake center;
b. retrieving medical records and prescription claims for the patient from an information warehouse;
c. analyzing the medical records and prescription claims to stratify the patient into a disease category;
d. establishing a network of therapeutic pharmacies, wherein each therapeutic pharmacy within the network is established in accordance with a wellness category;
e. classifying the patient prescription to the patient wellness category, and routing a pharmaceutical prescription to a therapeutic pharmacy within a network; and
f. filling and dispensing the prescription to the patient.

BRIEF DESCRIPTION OF THE DRAWINGS

Figure 14:
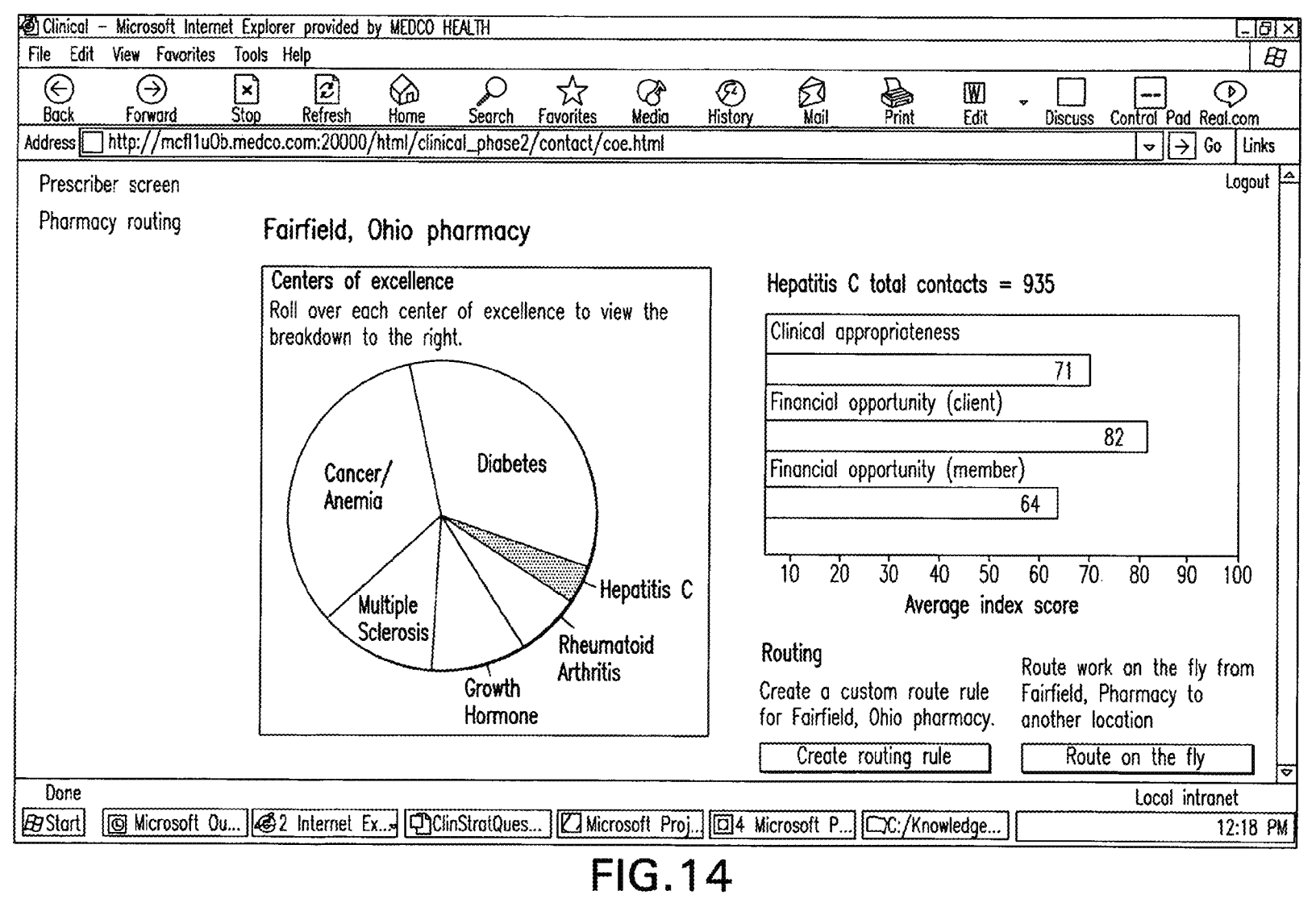

FIG. 14 is a screen shot of a system of the present invention wherein a routing capacity chart of a particular pharmacy is illustrated;

FIG. 17 is a screen shot of a system of the present invention wherein routing dimensions for sending the prescription to a suitable pharmacy is illustrated;

FIG. 19 is a screen shot of a system of the present invention wherein a patient's general information and open prescription orders are illustrated;

FIG. 20 is a screen shot of a system of the present invention wherein another patient's general information and open prescription orders are illustrated;

FIG. 21 is a screen shot of a system of the present invention wherein a patient's known medical conditions and directions for new medication may be coded into the system; and FIG. 22 is a screen shot of a system of the present invention wherein a chart of a patient's open/unresolved prescription orders and medication information are illustrated.

DETAILED DESCRIPTION OF THE INVENTION

Figure 1:
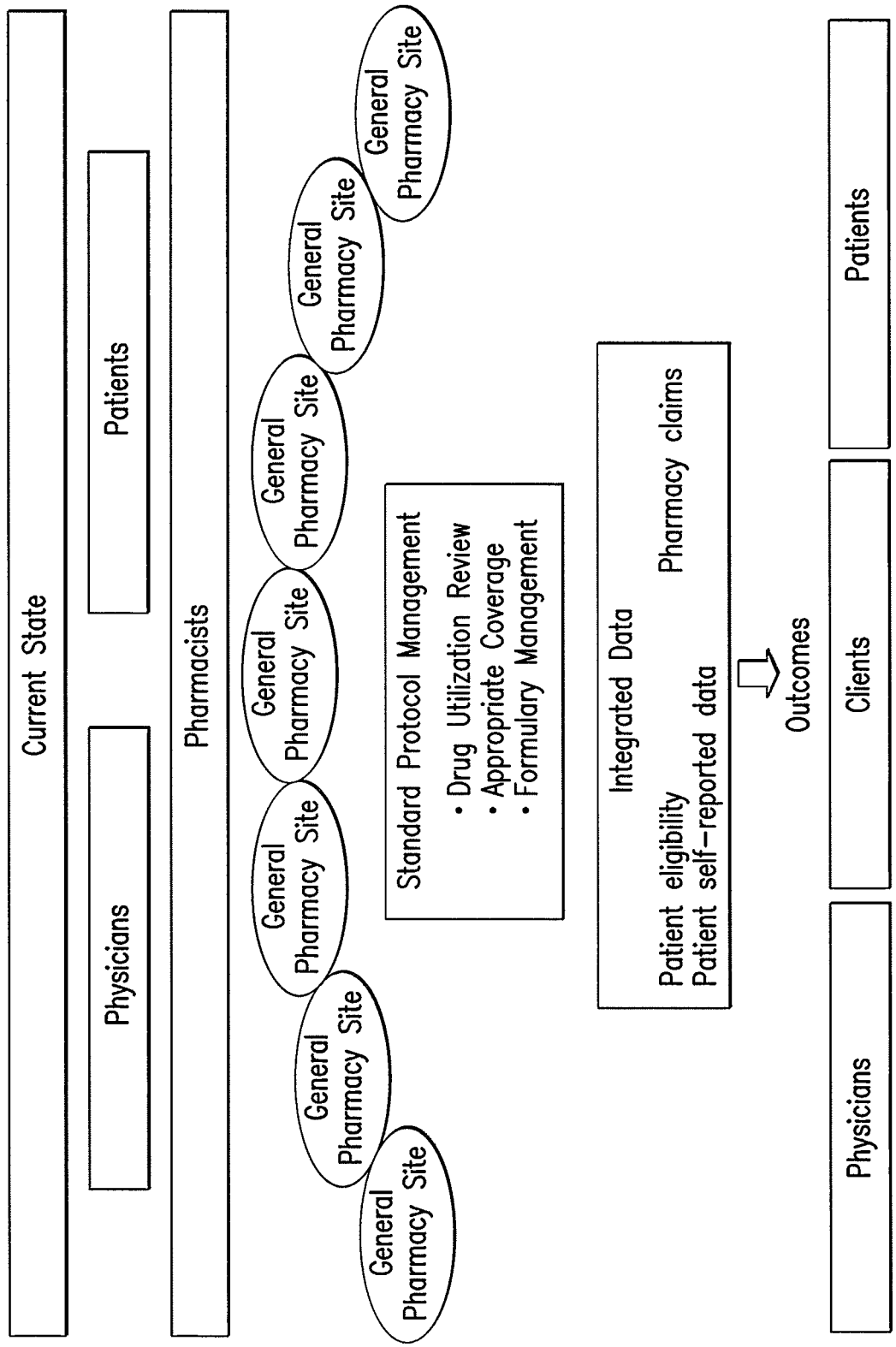
FIG. 1 is an illustration of a clinical approach of the method of the present invention to stratify patients into wellness groups.
Figure 2:
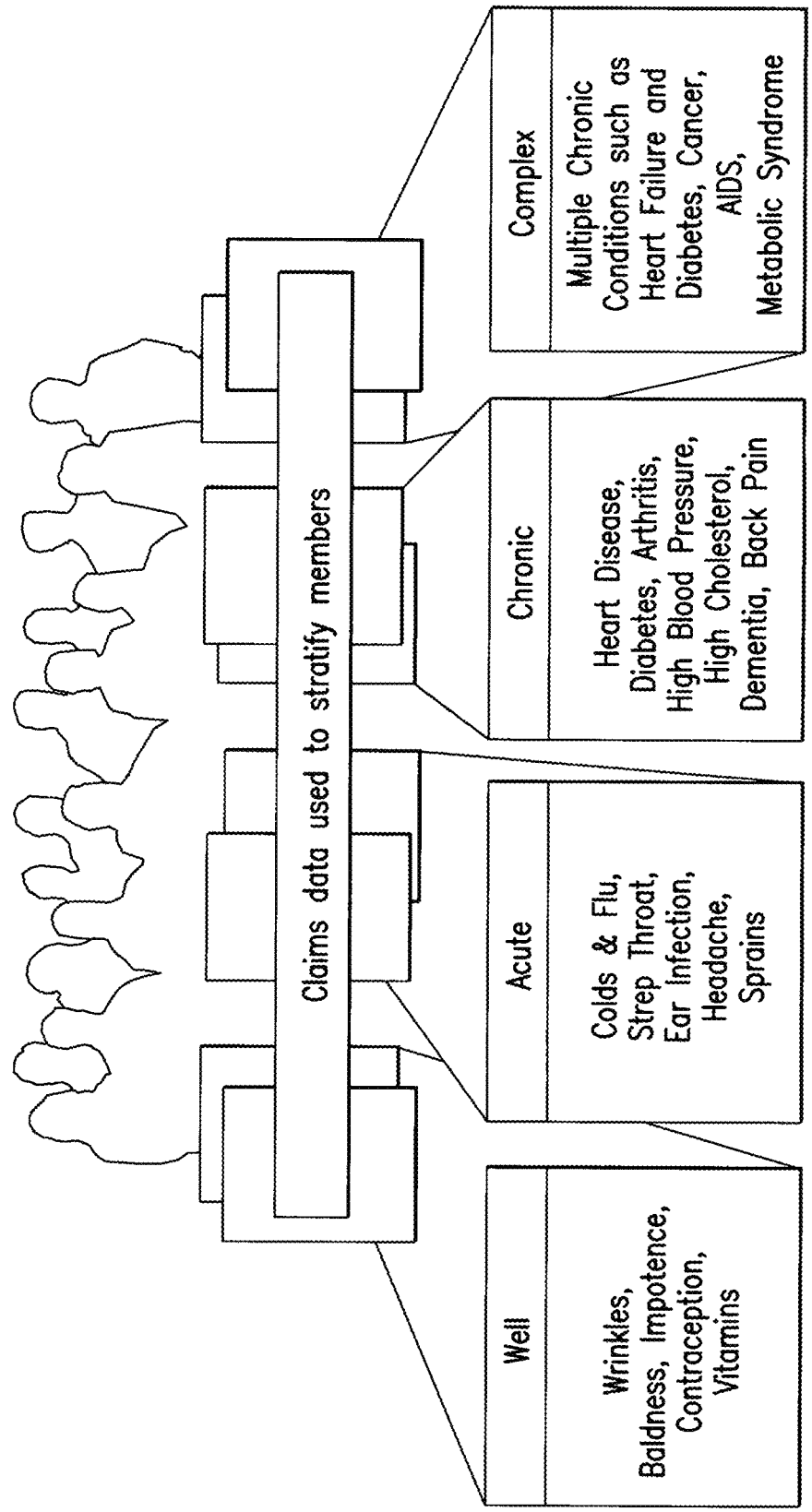
FIG. 2 is an illustration of a categorization of individual therapeutic centers within the network of therapeutic centers of the present invention to service disease groups.

The present invention is directed to a system and method for establishing and operating a plurality of individual therapeutic pharmacies within a pharmaceutical network, wherein each therapeutic pharmacy has been established to fill and dispense prescriptive medication associated with particular disease and disease states. In one embodiment of the invention, members of a particular health insurance plan may be classified into various states of wellness. FIG. 1 provides an illustration of four (4) possible classes of a state of wellness that may be utilized to segment members, e.g., well, acute, chronic and complex. The classification of 'well' may be associated with conditions that are least severe, e.g., wrinkles, baldness, impotence, etc., while an 'acute' state may be associated with colds and flu, strep throat, ear infection, headaches, sprains, etc. A more serious state of 'chronic' may be associated with heart disease, diabetes, arthritis, high blood pressure, high cholesterol, dementia, back pain, etc., while 'complex' conditions may be associated with life threatening conditions such as heart failure, diabetes, cancer, AIDS, metabolic syndrome, etc. In another embodiment of the invention, members of a particular health insurance plan may be classified into various disease conditions. FIG. 2 provides an illustration of such a classification, wherein the disease may be partitioned as neurology/psychiatry, pulmonary, cardiovascular, diabetes, gastroenterology, oncology/hematology, rare diseases, etc. The figure provides an illustration of a further classification of each aforementioned disease state, wherein the classification of diabetes may contain the conditions of Type I, Type II, pediatric, metabolic syndrome, complex, etc. Accordingly, within a network of therapeutic pharmacies, wherein a plurality of individual therapeutic pharmacies operate to fill and dispense prescriptions, one or more of the individual pharmacies may be strategically established based on a state of wellness or for one or more particular diseases. Pharmacist within each individual therapeutic pharmacy may be specifically trained to provide services for particular states of wellness or disease categories associated with the individual therapeutic pharmacy within the network of pharmacies. To determine whether a patient is complying with the administration of medication, or if there are possibilities of utilizing alternative, less costly medications, a clinical score may be generated by an analysis of patient claim history, formulary rules, and medical records. For example, a high clinical score, e.g., 10, may be interpreted as high possibility of reducing patient cost by prescribing alternative medications, e.g., generics, while a low clinical score, e.g., 2, may be interpreted as low possibility of reducing patient costs and that the patient is efficiently utilizing all formulary advantages associated with a particular health insurance plan.

Figure 3:
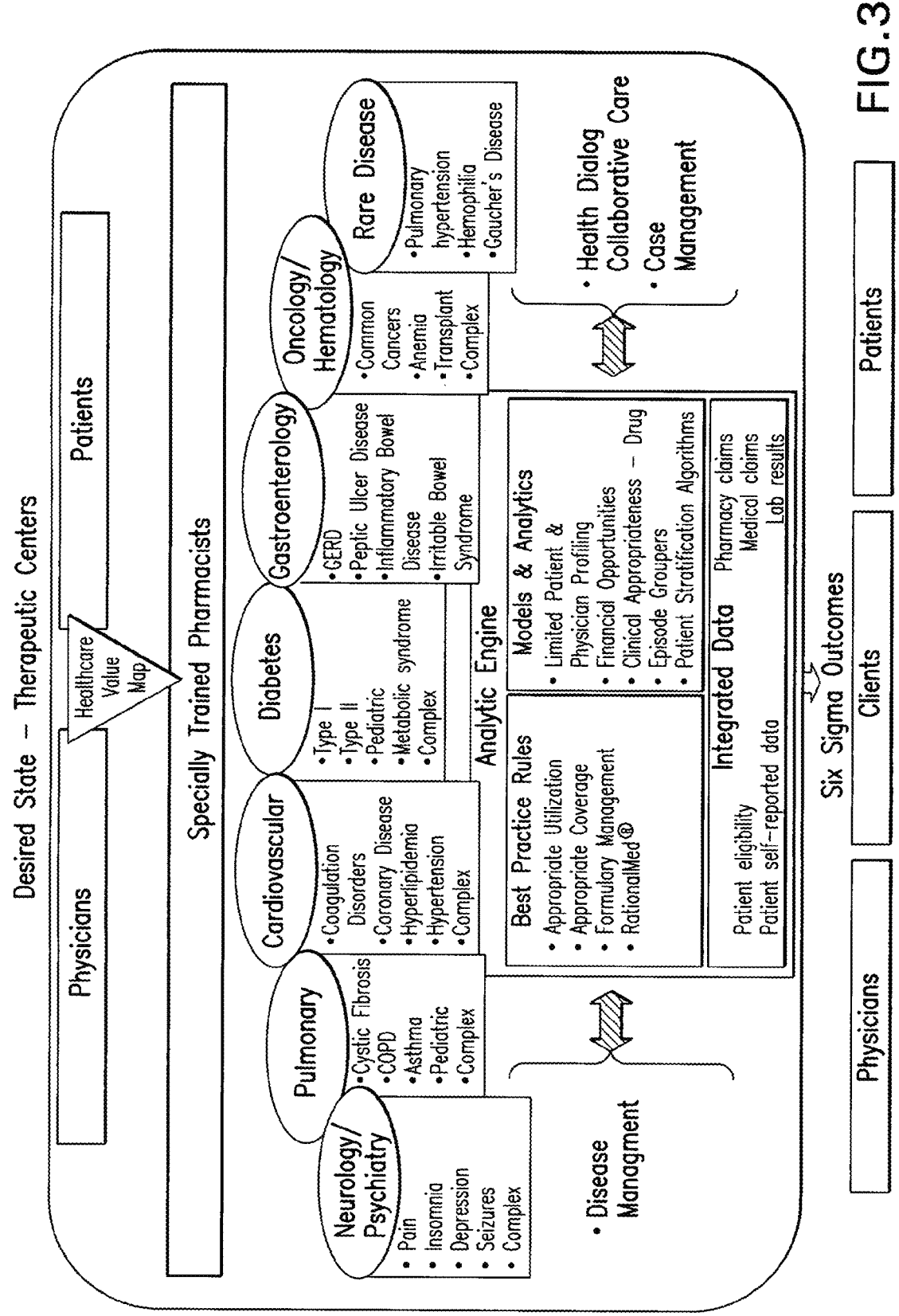
FIG. 3 is an illustration of a method of making clinical decisions of the present invention.

FIG. 3 illustrates a typical patient-physician-pharmacist relationship embodiment of the present invention. In accordance with the figure, the patient has been diagnosed with several medical conditions, including diabetes, high blood pressure, high cholesterol, migraines, coronary disease, and back pain. The attending physician has diagnosed the conditions and may prescribe one or more medications for treatment. Upon receiving a prescription, the system of the present invention will provide 'clinical decision support' comprising reviewing 'best practice rules' and establishing 'model and analytics' to stratify the patient in one or more wellness or disease categories. The 'best practice rules' comprise determining whether there is appropriate coverage under a health insurance plan for the prescription, within the patient's formulary, a drug utilization review, and potential adverse effect with other medications. The 'model and analytics' comprise profiling the patient-physician relationship to determine if the physician prescribes additional medication for the patient, whether financial opportunities exist to reduce plan and patient costs, the clinical appropriateness of utilizing the medication for the particular ailment, and stratification of the patient into one or more wellness and/or disease categories.

Figure 4A:
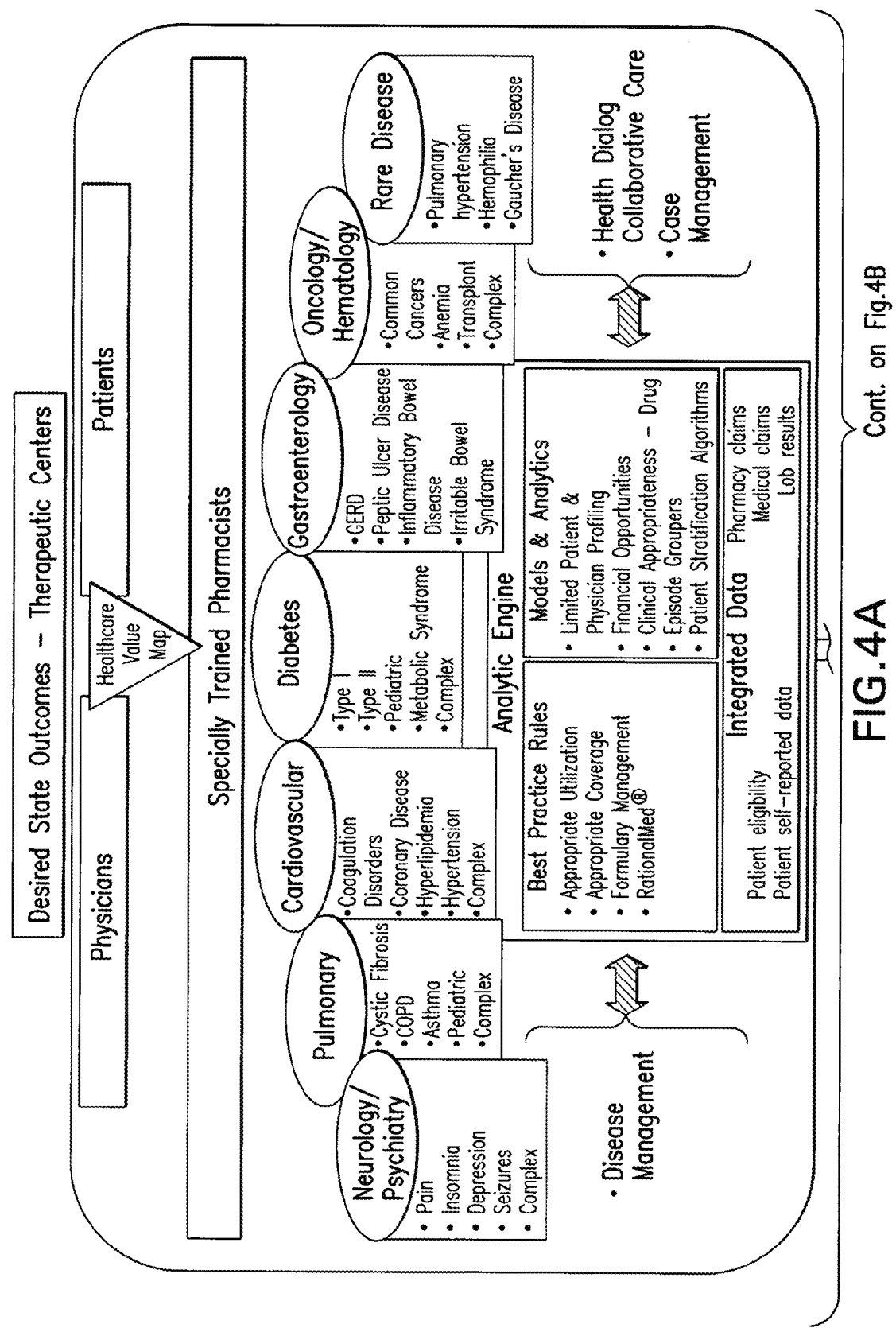
FIGS. 4A and 4B are schematics of the system of the present invention suitable for practicing the clinical method of the present invention.
Figure 4B:
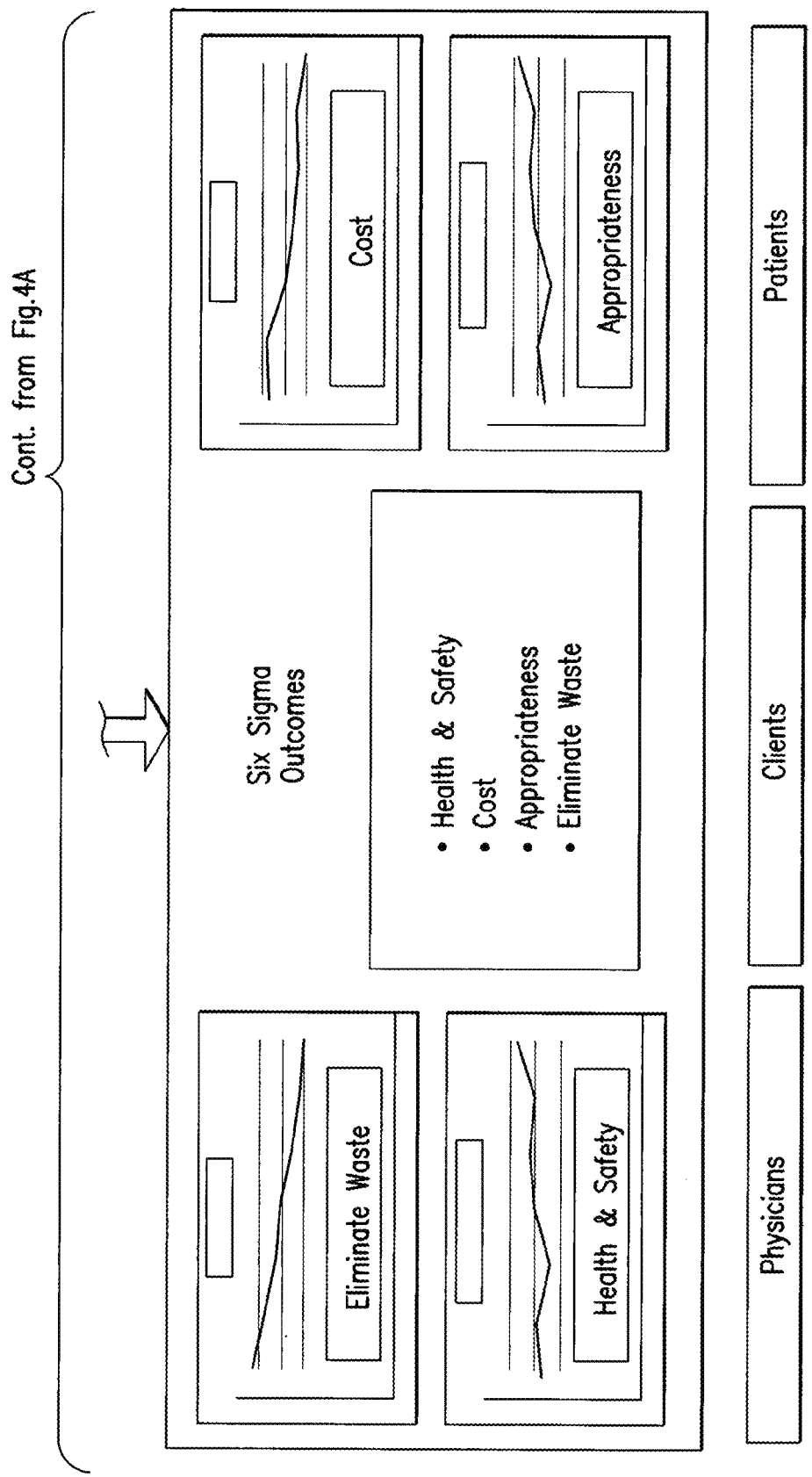

FIG. 4 is a schematic of the system of the present invention, wherein a prescription (010) may be provided by a prescriber, e.g., physician, to a patient, wherein the prescription is directed to medication suitable for relieving an ailment or disease suffered by the patient. The patient may submit the prescription to Prescription Receiving unit (100) for filling and dispensing to the patient. The Prescription Receiving unit is in electronic communication with a Patient On-line Authoritative Record unit (200) (POLAR) and request necessary information about the patient prior to processing the prescription. Similarly, POLAR, through electronic connections with a Patient Stratification unit (300) and a Clinical Score unit (400), is in electronic communication with an Information Warehouse database (500), suitable for receiving, storing and transmitting patient medical record and/or prescription claim information. POLAR will contain data files for all patients participating in a health insurance, prescription plan. Information Warehouse database may be continually updated with new medical records and prescription claims as they become available. The information may include patient identifiers and data, e.g., names, addresses, patient identifiers, insurance providers, co-pay information, formulary information, prescription order histories, medical records, etc. The clinical scoring and stratification process will continually execute and update to determine a patient's stratification/wellness category and clinical score, which is subsequently stored in POLAR for use by Prescription Receiving or display by a user, e.g., pharmacist or claims representative, and for making a therapeutic routing decisions. After POLAR collects data regarding patient stratification and clinical score, it electronically communicated with Formulary Rules database (600) to determine if the prescription is within the patient's insurance coverage, formulary and rules. Formulary Rules is also capable of performing drug utilization reviews and screening for potential adverse effects of the prescribed medication with other medications the patient may be administering. After POLAR has collected the necessary data required to fill the prescription, it notes any unresolved protocols from the Information Warehouse or Formulary Rules is inconsistent with the prescription, e.g., lack of insurance coverage, medication outside of the formulary, potential adverse effects with other medications, etc. and transmits the information to POLAR which relays the collected information to Prescription Receiving for merging with the prescription. Afterwards, the merged prescription and patient information is electronically forwarded to a Optimal Workflow and Load Balancing unit (700) (OWLb), wherein OWLb examines the POLAR data to determine the optimal Therapeutic Pharmacy (800) and pharmacist (900) within that Therapeutic Pharmacy suitable for handling the prescription order. Thereafter, the order will be assigned to the Pharmacist and electronically appear on her computer task screen. If POLAR has noted any unresolved protocols, the Pharmacist may transmit the prescription order to an Integrated Contact Management unit (1000) (ICM) for resolution, wherein ICM will communicate with POLAR to gather additional patient stratification and clinical score information the Pharmacist may need for display on the pharmacist's computer task screen. This additional data is may be used to assist the Pharmacist in resolving open protocols on that patient's order and allow the order to eventually be filled and dispensed.

Prescription Receiving (100)

In accordance with one embodiment of the present invention, pharmaceutical prescriptions may be received at a Prescription Receiving (010) for a network of therapeutic pharmacies, wherein individual therapeutic centers, i.e., therapeutic pharmacies, within the network are established based on patient stratifications and/or therapeutic conditions. The prescription (010) may be received by Prescription Receiving (100), wherein the prescription contains patient identification information, physician and prescriber information, as well as type of medication, and medication quantity and concentration, etc. Generally, the prescription may be received in electronic form, but if necessary, a hard-copy prescription may be scanned or converted to electronic form by conventional means and fed into the Prescription Receiving unit of the present invention. Prescription Receiving may resolve administrative protocols, e.g., patient enrollment and eligibility, prior to processing the prescription in the system of the present invention. Upon resolution of any administrative protocols and conversion into an electronic form, if necessary, the prescription may be fed into the system for filling and dispensing.

Patient On-Line Authoritative Records (Polar) (200)

POLAR, is a data store, which maintains information relevant at the patient level. This includes Patient Stratification and Clinical Score data that is used by OWLb for determining optimal work assignments and displaying in Integrated Contact Management. POLAR may be periodically updated by the Information Warehouse to reflect changes in the clinical scores and patient stratification information. POLAR is capable of creating an individual artificially generated number (AGN) which is a unique person identifier that enables the organization to track a person's demographic, clinical and communication history as well as financial activity at the individual level. The individual AGN may be assigned in a background process when data is moved to the Information Warehouse. POLAR receives data from Patient Stratification (300) and Clinical Scores (400), and analyzes the data to assign an AGN suitable for routing a prescription to a selected therapeutic pharmacy within the network of therapeutic pharmacies particularly established to provide specialized pharmaceutical care to a patient of a correlating wellness category. The AGN for a patient is transmitted to an Optimal Workflow and Load Balancing (OWLb) system (700) where it is utilized. POLAR may continuously receive data from Patient Stratification and Clinical Score (400) for generation of the AGN.

POLAR stores and updates data from multiple sources and supports current postal addresses and e-mail addresses and telephone numbers for patients, as well as date of birth, deceased status, gender, demographic and geographic information, medical conditions, drug allergies, HIPAA privacy consent and authorizations. POLAR provides a data quality dashboard to help determine the integrity of the data, e.g., confirms accuracy of data, provides tracking analyses detecting potential inconsistencies in data patterns (system errors, incomplete, or irrelevant data), and improves identification and targeting opportunities. POLAR populates IW for decision support analyses and reporting. POLAR provides a wide variety of software applications with the core objective to increase data quality and content for clinical data used by DUR, Home Delivery Pharmacies, Customer Service, and Internet applications. These various software applications interface with two main clinical data stores: Patient Profile VSAM files and the NRXPRF Idiosyncrasy table. The Patient Profile VSAM files are the central clinical repository for all ICD-9 codes for Medical Conditions and NDC codes for Drug Allergies. The Patient Profile VSAM files are updated daily by Home Delivery Pharmacy applications during prescription processing, Customer Service application systems, Internet, Health Assessment Questionnaires responses from our Members, and Client feeds. All clinical information contained in both main data stores may be used by DUR during prescription processing. There are a wide variety of POLAR software applications that interface with these data stores, internal operational system areas, external vendors, and clients. POLAR software applications encompass development of periodic patient profile ICD-9 or NDC files from external vendors, internal departments, and client feeds. Development of a centralized repository for clinical codes and descriptions that are used on various Home Service Delivery and Customer Service screens. These tables control what descriptions, options, codes, etc. are displayed on various customer service type screens as well as what codes should be passed to POLAR. POLAR is capable of processing mandatory communications, such as Health Assessment Questionnaires, Notice of Privacy, Authorization, and Consent forms. The system manages the entire solicitation life cycle for mandatory communications from the initial entrance into the system, releasing records to internal or external vendors for solicitation distribution, vendor feedback confirmations, and response tracking The new POLAR Communication System also has been designed to allow substantial depth for custom fulfillment needs. POLAR stores current and historic address and phone number information for individuals. Additionally, the address databases may be structured to store permanent and current address and phone number information. All addresses in POLAR may be processed through CODE-1 data cleansing, to ensure that POLAR has deliverable contact information. In addition to existing book of business address cleansing efforts, POLAR either may receive address and phone number updates via customer service, MMRx, Internet applications, health management systems, managed care operations, client systems/projects, InterDirect—vendor address cleansing/lookups, Health Assessment Questionnaires, etc. In addition to 'pushing' address and phone number information to POLAR, many of the operational systems listed above use POLAR to 'pull' the most current demographic information for an individual upon demand. Additionally, the demographic information retained in POLAR is used in developing business strategies for increasing the overall quality of our health care products and person-centric services. POLAR stores current and historic preference information for individuals in its databases. Currently, preference information encompasses an individual's desire to either Opt-Out or Opt-In to a health product or service, refill reminder and 'never ask' preferences, as well as E-Health preferences. Future capability includes the ability to retain how and when an individual prefers to be contacted (i.e., mail, E-Mail, telephone, or facsimiles) as well as prescription bottle types, lifestyle and behavioral factors.

In addition to 'pushing' preference information to POLAR, many of the operational systems listed above use POLAR to 'pull' the most current preference information for an individual upon demand. Additionally, the preference information retained in POLAR is used in developing business strategies for Medco Health and increasing the overall quality of our health care products and person-centric services. POLAR Correction and Distribution Workstation (CDW) is an operational based capability that may be used to process member information updates on POLAR data stores. The system manages information updates for SSN to non-SSN transfers, Patient Profile zero AGN corrections, and AGN Over/Under match corrections. The POLAR Patient Profiles contains allergy and medical conditions for our members. This information is used by DUR during drug utilization review to ensure there are no adverse drug interactions. Data in the patient profiles is stored at the Individual AGN level, along with various member information (member number, carrier, date of birth, etc.). On occasion, the Individual AGN is unknown at the point of updating the profile, and an attempt must be made to later derive one for the profile record to be used. These 'zero AGN' records are read in from the patient profiles on a nightly basis and processed via the CDW front end. POLAR Patient Profiles contains allergy and medical conditions for our members. This information is used by DUR during drug utilization review to ensure there are no adverse drug interactions. Data in the patient profiles is stored at the Individual AGN level, along with various member information (member number, carrier, date of birth, etc.). On occasion, the Individual AGN is assigned incorrectly (either the same AGN is assigned to multiple different people, or multiple different AGNs are assigned to the same person.). These over/under match records are identified by eligibility and provided to all areas of the company. The CDW user takes this information and performs the necessary updates to the core POLAR data stores. A full audit trail of the correction for each AGN and the data store where the information was modified is stored within the CDW.

Patient Stratification (300)

Patient Stratification is a unit within the system of the present inventions suitable for computer analyses of patient medical record and prescription claim information contained in the Information Warehouse (200) to determine the potential for utilizing the method and system of the present invention, wherein the database contains sufficient information to perform analyses. If sufficient medical record and prescription claim information is available to perform a patient analysis, wherein the patient will be stratified into one or more wellness categories, e.g., well, acute, chronic, complex, etc. Each wellness category may be further defined, for example, by the past medications prescribed to a patient, illnesses, and diseases states. For example, FIG. 2 illustrates one embodiment of the invention of stratifying patients into wellness categories, based upon disease states, into a plurality of wellness categories, wherein less serious diseases may be defined as well and acute, and more serious diseases may be defined as chronic and/or complex. For example, FIG. 3 illustrates several disease state defined in accordance with established medical disease categories, e.g., neurology/psychiatry, pulmonary, cardiovascular, diabetes, gastroenterology, oncology/hematology, rare disease, etc., and patients may be placed into one or more disease states based upon the patient's current medical diagnosis. While the disease states mentioned herein are examples of methods of classifying patients, other methods and categories will become apparent to those skilled in the art. Nevertheless, the individual therapeutic pharmacies of the network of therapeutic pharmacies of the invention will be segmented based upon the categorization utilized for patient stratification, wherein the individual pharmacies will be established to fill and dispense prescriptions for one or more categories of diseases. Patient stratification results may be available for transmittal to and storage in POLAR.

Clinical Score (400)

Clinical Score is a unit of the invention wherein a numerical value assigned to a patient based upon the quality of pharmaceutical services received, wherein a low score represents very good services and a high score represents poor services. For example, if a patient prescription claims history reveals that the patient suffers from wrinkles, baldness, impotence, utilizes contraceptives and/or is vitamin deficient, in accordance with the method, the patient's score may be established as Well. If the patient prescription claims history reveals that the patient suffers from occasional colds and flu, strep throat, ear infection, headaches and sprains, the patient may be scored as Acute. Further, if the patient prescription claims history reveals that the patient suffers from heart disease, diabetes, arthritis, high blood pressure, high cholesterol, dementia and/or back pain, the patient may be scored as Chronic. If the patient claims history determines that the patient displays multiple chronic conditions such as heart failure and diabetes, cancer, AIDS and/or metabolic syndrome, the patient may be scored as Complex. Clinical Score modeling may take the form of many conventional methods. In one embodiment of the invention, for each complex patient, calculate the points for each of the 4 clinical indexes below. Add up all of the scores for a given patient and retain a total Clinical Score. Assign a reason code or explanation for each clinical index which can be passed to POLAR with the total clinical score.

Clinical Care Opportunities:

a) Polypharmacy

Number of Medications

Evaluate each patient's paid pharmacy claims history for the last 180 days to determine the number of unique drugs (HICL) listed.

Score: Provide 1 point for each unique drug (HICL) listed in the patient's paid claim history for the last 180 days. Sum the number of points (to a maximum of 30) for a total medication score.

Reason code: List the number of drugs found in the last 180 days, e.g., patient taking "X" drugs in the last 180 days.

b) Concurrent Drug Utilization Review:

Home Delivery (HD) CDUR

Evaluate each patient's paid pharmacy claims history for the last 180 days for the listed CDUR alert protocols with the specific resolution codes. See Appendix B.1 for Home Delivery CDUR protocols, resolution codes and points.

Score: For each patient, count the points assigned to each selected HD CDUR Protocol with specific Resolution codes, e.g., for protocol Seniors—excessive daily dose (SURHD), resolution code dispense as written—no call (DAWNC) –2 pts., Seniors drug disease (SURMC), resolution code dispense as written, no contact w/MD spec time (DAWNC) –2 pts.=4 and add them together with the Retail CDUR points for a total CDUR score for the patient.

Reason code: For each patient, select the most current 3 HD CDUR protocols that have the resolution codes with the highest point values assigned to each, e.g., Seniors—excessive daily dose (SURHD), resolution code dispense as written—no call (DAWNC) –2 pts.; Seniors drug disease (SURMC), resolution code dispense as written, no contact w/MD spec time (DAWNC) –2 pts. Display the resolution date, protocols and resolution codes in English & the applicable drug names for the respective protocols.

Retail CDUR

For each patient, count the 2 points assigned to each selected Retail CDUR with an 02 override code and add them together for a total Retail CDUR score. Then add them to the HD CDUR score for a total CDUR score for the patient.

c) Retrospective Drug Utilization Review & RationalMed:

RDUR, Therapy Optimization & RationalMed: Therapy optimization and omission of therapy Evaluate each patient's paid pharmacy claims history for the last 180 days for the listed therapy optimization and omission of therapy enhanced rule (SDI and SCI) alerts fired.

Score: Each selected RDUR alert fired receives 2 pts. Add up all points for total RDUR-RM score for the patient Reason code: Select the 2 most current alerts fired e.g., Treatment of stable angina (SDI 002) & ACE inhibitor or ARB for the prevention & treatment of diabetic nephropathy (SDI 004). Display the date the rule was triggered, drug(s) name/NDC (in English) and the letter text from the physician letter template.

Source: IRHM_Proddb_v.protocol_event; Protocol Management Decision (PMD), tables in IW "Event" RDUR files updated quarterly; RationalMed files updated monthly d) Late to Fill:

Persistency—Length of continuous medication

Non-persistence—A late-to-refill that exceeds 60 days from the end of the last fill and is still present at the current run date. Discontinuance of persistency flag—Turn off the patient's persistency flag for a specific drug chapter if (latest fill date+days supply+180–1)<current run date then patient is discontinued for a particular therapy Priority 1. Anti-arrhythmic agents: 4.1
2. Anti-hypertensive therapy: 4.5
3. Diabetes: Insulin therapy 7.5.1; oral hypoglycemic agents 7.5.2
4. Lipid-lowering agents: 4.6
5. Anti-platelet drugs: 4.4.2

Late to Fill detail.

Score: If non-persistent with any of the above drug chapters, assign a Yes=5 pts.; If persistent with any of the drug chapters, assign a No=0 pt.

A patient can have 0-25 points depending on the number of Yes answers. Add all of the Yes answers for a total persistency score for the patient.

Discontinuance of therapy will be assigned a score of 0 points for the purpose of calculating the total persistency score.

For IW, the requirement for reporting will be to store the score for all 5 drug chapters for each patient with a way of differentiating between those who are persistent and those that have dropped off (0 points).

Reason code: Select the most current 2 drug chapters that are non-persistent e.g., diabetes 7.5.2 & antihypertensive therapy 4.5, and list each of them with the explanation "Late to refill->60 days", the appropriate drug(s)/NDC (in English) and run-out date (latest fill date+days supply+60–1). If more than 2 are non-persistent, use priority as listed above. Number 1 has the highest priority and should be selected first and so on.

Financial Savings Opportunity Indexes

Use existing programs, their business rules and drug lists:

New Prescriptions

Co-pay and client savings opportunities will be based on existing Managed Care programs, using the Managed Care system and interventions methodology.

An interface between ICM and Managed Care system, using screen-scrape technology, will provide the pharmacist with access to and detail on the financial opportunities available through the Managed Care programs. The pharmacist will view and resolve the opportunities in the Managed Care system. Programs include:

Therapeutic interchange;
    Non-preferred to preferred brand name drugs; and
    Brand name drugs to generics;
    Coverage Management;
    Traditional Prior Authorization;
    Step Therapy; and
    Dose Optimization-Coverage;
    Formulary Coverage Review (FCR)

Existing Prescriptions

Therapeutic Interchange;
    Non-preferred to preferred brand name drugs; and
    Brand name drugs to generics
    Retail to Mail Conversion
    "Home Delivery Advantage" Program
    Therapeutic Interchange;
    Non-preferred to preferred brand name drugs; and
    Brand name drugs to generics The Managed Care interface will provide the pharmacist with detailed information on patient specific 'ProActive' financial opportunities. The pharmacist will view and resolve the opportunities in the Managed Care system.

Home Delivery Advantage

Retail to Mail Conversion Opportunities

Identify (at a drug specific [NDC] level) any retail prescriptions for targeted maintenance drugs for the most current 3 months. Using current pricing, eliminate opportunities that generate a negative client savings.

Use Home Delivery Advantage business rules to identify the retail to mail conversion opportunities. A Patient Stratification opportunity for conversion from retail to mail would be where there has been no activity related to a channel shift from retail to mail e.g., with no response to a letter or HD Advantage decline outcome code.

Source: This could include new patients, new patient/drug combinations, or updates to existing opportunities. The load file should be unique on Group Operational ID (Group)+Client Membership ID (Member Number)+Relationship Code (Relationship)+Person Number (Person Number)+Mail NDC (NDC). Each opportunity includes a CORE Opportunity ID and CORE Opportunity Sequence Number.

Information Warehouse (IW) (500)

Information Warehouse is a database comprises patient medical record and prescription claim information. The database, continually updated with new patient information, may contain patient information of previous medical record and prescription claims compiled over a chosen period of time and may include medical records, prescription plan, claims history, home delivery purchased, retail purchased, refill history, prescription costs, prescription co-pay history, etc., wherein the information is suitable for determining Patient Stratification (300) and Clinical Score (400). Information Warehouse is charged with providing clinical and financial business information that encompasses the claims data available. Information Warehouse is a data repository that supports clinical, financial analysis and reporting of claim activity. It is suitable for storing about 36 months of internal and external claims history and client, patient, provider (prescriber and pharmacy) and drug data related to the adjudication of those claims. Aside from making claims history available, the Information Warehouse provides a unique patient identification feature. The patient identification process uses third-party data cleansing software to identify an individual across the system. The process assigns a unique patient identifier, regardless of whether she is eligible in multiple groups or have had interrupted coverage. It is this capability, along with the capability of analyzing medication usage and costs over time, that make the warehouse the optimum source of data for targeting programs developed in the company. Information Warehouse responsibilities include the identification, definition, modeling, and sourcing of all data that are stored therein. Architecturally, the Information Warehouse utilizes specialized Massively Parallel Processing (MPP) hardware and system software that decomposes database requests into smaller sub-units that can be processed in parallel. This architecture enables the rapid processing of large volumes of data with elapsed times several orders of magnitude less than would otherwise be possible.

The 'claim subject area' of IW contains facts about the claims submitted by client-members in conjunction with the dispensing of medical products. The main data category within this subject area is a set of physical claim tables, organized by client, which house claims data. Each claim has relationships to the reference data in each of the other subject areas. For example, a claim will point to the relevant prescriber in a 'provider subject area table'. Similarly, a claim will point to the relevant product, group and member in the 'drug, client and patient subject areas', respectively. As a result, the amount of reference data kept in the central fact table may be reduced. This subject area includes numerous attributes related to the claim type, prescription, pricing, dispensing, refills, cost components, adjudication, adjustments, co-pay, deductible, etc.

The 'client subject area' contains reference data about the client organizations that currently use or recently used the pharmacy benefit management services. The main data categories within this subject area are the multi-level operational units comprising a client organization (client organizational ids, carriers, contracts, groups, benefit groups and related groups) and the high-level products and services that a client has contracted for (e.g., disease management programs). Each type of relationship that links the different client operational levels is shown as a separate hierarchy (e.g., client sales hierarchy, client billing hierarchy, etc.). This client subject area includes various attributes that characterize a client's status, organizational classification, eligibility rules and special processing requirements. It also identifies the claim table where a client's claims are maintained.

The Drug Subject Area contains reference data pertaining to pharmaceutical and other products that have been approved for sale by the Food and Drug Administration (FDA). The main data categories within this subject area are the medical products from manufacturers, product pricing and formularies, and their organization into therapeutic chapters and subchapters. Medical products include both drugs and certain non-drug products, such as medical supplies. A drug product has numerous physical attributes, such as strength, dosage form, administration route and package size. A drug product also has identification attributes, such as numeric codes and names. Drugs are classified according to criteria that reflect the generic formulation, generic market status and therapeutic class. This subject area includes the classification of drugs, their therapeutic properties and uses, and the classification of diseases and medical conditions.

The 'patient subject area' contains reference data about the active and retired employees of clients who receive pharmacy benefits. The main categories within this subject area are memberships, members and patients. Membership identifies the members covered under a particular benefit plan. A member is an individual covered under a membership, including the originating subscriber and any dependents to which benefits have been assigned. A patient is an individual who may receive benefits under one or more plans regardless of the individual's carrier, contract or group identification. This patient subject area includes membership and member identifiers, coverage attributes and member attribute data. It also identifies a member's primary care provider and members within each carrier for whom claims have been submitted.

The 'provider subject area' contains reference data about the individual practitioners and provider organizations involved in providing health care services of interest, e.g., writing prescriptions for and dispensing drugs. The main data categories within this subject area are the individual practitioners authorized to write prescriptions (also known as prescribers) and the pharmacies that process and fill the prescriptions. Practitioners may be classified by type of medical practice and medical specialty. Provider organizations may be classified by type of pharmacy, organizational status (pharmacy or pharmacy organization) and organizational affiliation (chain, franchise or unaffiliated). This provider subject area includes the various identifiers used to identify providers, as well as provider attribute data, some common to both pharmacies and practitioners, such as name and address, and some specific to one type or the other.

Formulary Rules (600)

Utilization Management shall implement a set of rules that enforce compliance with the SPCR for a particular therapy. In general the SPCR shall determine the timeline, type of intervention and skill set required for a type of intervention as shown in the example in the table below:

| Call Name | Call From | Call To | Rx Status | Timing | Purpose and Call Content |
| --- | --- | --- | --- | --- | --- |
| Initial Patient | RN/PCR | Patient | New | Upon receipt | Delivery/Admin Logistics Storage requirements Offer to counsel Schedule Initial Patient Administration call, if necessary Send starter packet |

-continued

| Call Name | Call From | Call To | Rx Status | Timing | Purpose and Call Content |
|---|---|---|---|---|---|
| Initial Patient Administration | RPh/ Nurse | Patient | New | Within 2 days post manifest date | Storage/Administration ADRs Compliance with drugs and monitoring |
| Follow-up Patient | RPh/ Nurse | Patient | Refills & Renewals | 3, 7, and 11 weeks post therapy initiation | Storage/Administration ADRs Compliance with drugs and monitoring Follow up |
| Therapy Confirmation Call-Patient | PCR | Patient | Refills & Renewals | Upon refill or renewal request | Delivery/Admin Logistics Storage requirements Offer to counsel Schedule Patient Follow-up Call, if necessary |
| Refill/Renew Patient | PCR | Patient | Refills & Renewals | 7 days prior to next refill (wk 23, 35) | Delivery/Admin Logistics Screening Offer to counsel Schedule Patient Follow-up Call, if necessary |

Prior Authorization Rules confirms that the incoming prescription is consistent with plan coverage provisions. At times it may be necessary to contact the prescriber to obtain additional information to confirm coverage. In the event the prescription is not covered by the patient's plan, a Patient Care Representative (PCR) will contact the patient and the pharmacist will abort the prescription.

DUR Rules compares the incoming prescription with the patient's prescription history to detect potential health and safety issues and interactions such as, drug to drug, drug to allergy, drug to disease, dosing and over-utilization. In the event a potential health and safety issue is detected by the DUR rules engine an alert is fired. The pharmacist or physician may override the alert, modify the prescription or abort the prescription. In the event the prescription is changed or modified the patient is notified.

Managed Care Rules identifies potential cost effective and clinically equivalent product opportunities (i.e., generic or preferred products). The opportunity is presented to the physician and if the physician changes the prescription to the recommended product, the pharmacist will change the prescription and the Patient Care Representative will notify the patient that the prescription was changed.

Prescription Fill Rules ensure that for specific a therapy regimen may require specific clinical information each time a prescription is refilled. In some cases it may be necessary to contact either the physician or the patient to obtain the required information. The rules that process this information may modify the therapy regimen. Examples of the type of rules that may take place are:

First Fill Rules

Aside from making sure all required patient information is present in the system, each CoE may have unique information requirements. For example, for Hepatitis C an important determination is the patient's genotype as well as the timing of the patient's therapy. Other rules deal with patient training, delivering the drugs and additional care as per SPCR (Standard Procedure & Counseling Resource). Some rules may require a contact with the physician or patient.

Second/Third Fill Rules

This time around the rules deal with a refill. If no active refills remain, the pharmacist must contact the physician for refill authorization. In addition, DUR, compliance issues, therapy related questions and need for additional patient support may trigger a physician or patient contact.

Fourth Fill Rules

The fourth fill (technically a refill) is similar to prior fill rules, except that the patient's viral load (in conjunction with genotype information) is taken into account and specific SPCR instructions for the fourth month are consulted and followed-up.

Bundle Contacts Rules

Bundling rules shall create queries that shall be executed against the contact database to group contacts that are consistent with the role and Center of Excellence (CoE) of the user that requested a bundle.

Prioritize Contacts Rules

Prioritize contacts shall provide the rules to determine which contact to first resolve. The rules prioritize contact based on time contact was outstanding and clinical and financial benefit.

Route Contacts & Balance Workload Rules

Workflow management shall manage skill set routing and load balancing rules that monitor the workload associated with a requesting skill set and if the resource is under utilized than the query for bundling will be modified to route the bundle to a compatible skill set.

Optimal Workflow and Load Balancing (OWLb) (700)

Figure 5:
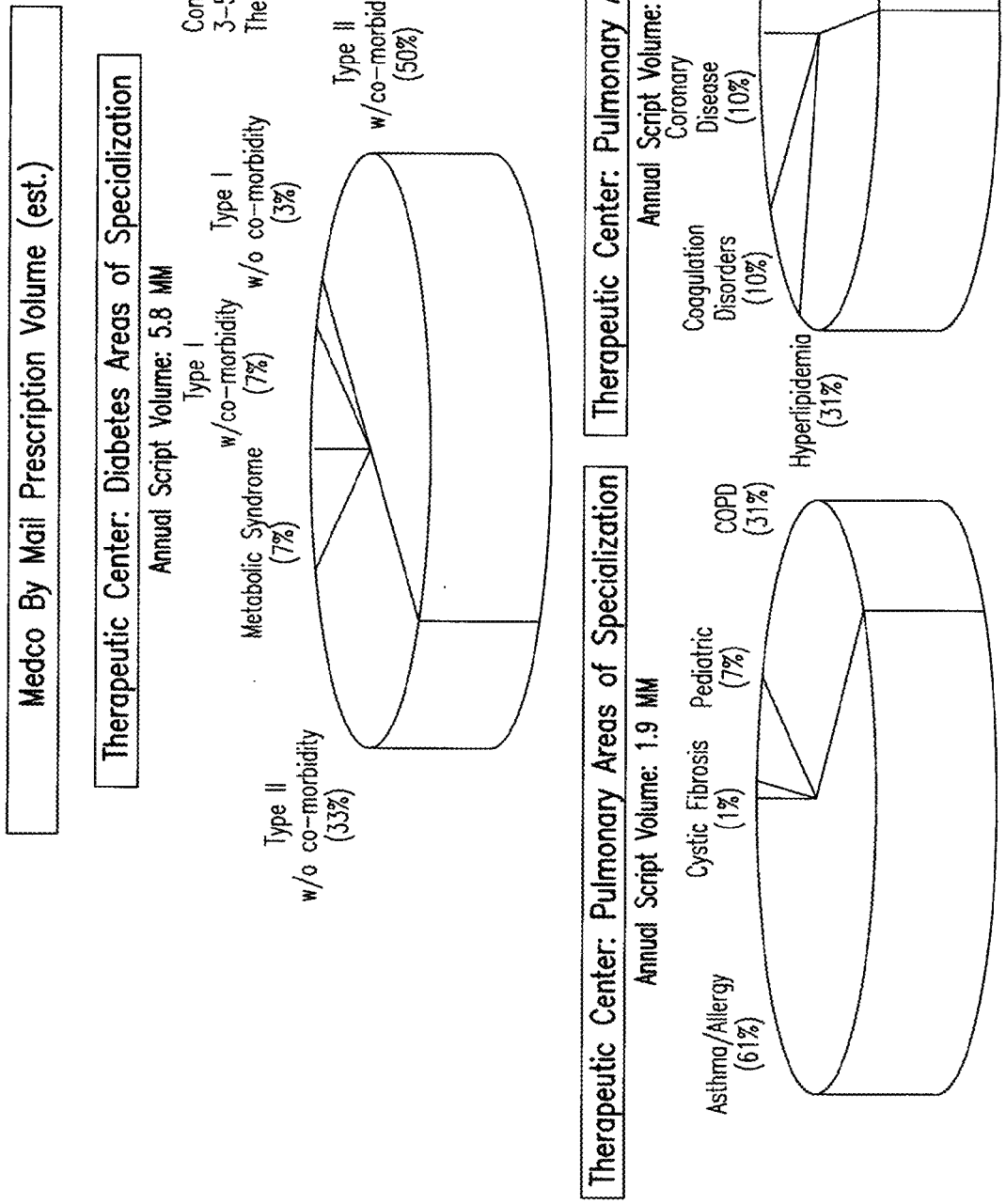
FIG. 5 illustrates a schematic of OWLb.

Referring to FIG. 5, OWLb is responsible for determining the optimal assignment of a patient's order to a person. OWLb takes a variant of perspectives into account when determining the optimal assignment. OWLb is suitable for receiving incoming prescriptions from prescription intake (100) and AGN data from POLAR, may utilize established criteria, rules and AGN data to prioritize and bundle prescriptions, and route the prescriptions to a therapeutic pharmacy particularly established, within the network of therapeutic pharmacies, to provide specialized services in accordance with AGN data, intervention type, pharmacy work load, prescription dates, etc. For example, if two or more therapeutic pharmacies within the network are suitable for filling a prescription correlating to particular AGN data, OWLb may select the pharmacy having the least workload when routing the prescription. From the perspective of the patient, OWLb considers the patient's stratification data and clinical score information from POLAR, along with a detailed examination of the patient's order and protocols. Upon examination of the patient and order, OWLb determines the appropriate Therapeutic Pharmacy to handle this order. From the perspective of the prescriber, OWLb considers the orders that are coming through the system and identifies orders belonging to patients from the same prescriber. Upon identifying these orders, OWLb bundles them together to minimize the number of contacts (i.e., phone calls) that are made to the prescriber during protocol resolution. From the perspective of the end user (i.e., the Pharmacist or Clerk), OWLb chooses the best person to handle the patient's order based on a variety of considerations. The end user may have many different skills ranging from clerical to professional, of which each user has a varying degree of ability. For example, one user may be considered an expert in one skill, while another user may only be a novice. OWLb takes all of these factors into consideration to determine the optimal person to handle a particular patient's prescription order, giving an optimal assignment of work for each end user. OWLb may receive a prescription, patient stratification and clinical score information from Prescription Receiving. OWLb reviews the information, based upon formulary and rule sets to select a therapeutic pharmacy (800) within the network of therapeutic pharmacies, and assigns the prescription to a pharmacist (900) within the selected therapeutic pharmacy to send the prescription to resolve any pharmaceutical protocols and filling the prescription. From the perspective of the overall environment, OWLb considers the current work load, schedule and productivity rate to perform load balancing. OWLb routes work where the end user is under utilized and attempts to maintain an even distribution of assignments. OWLb considers all of this telemetry data to perform an optimal assignment of a patient's order to an end user, which results in less contact with the prescriber, lower cost of prescription handling, and improved care.

Figure 6:
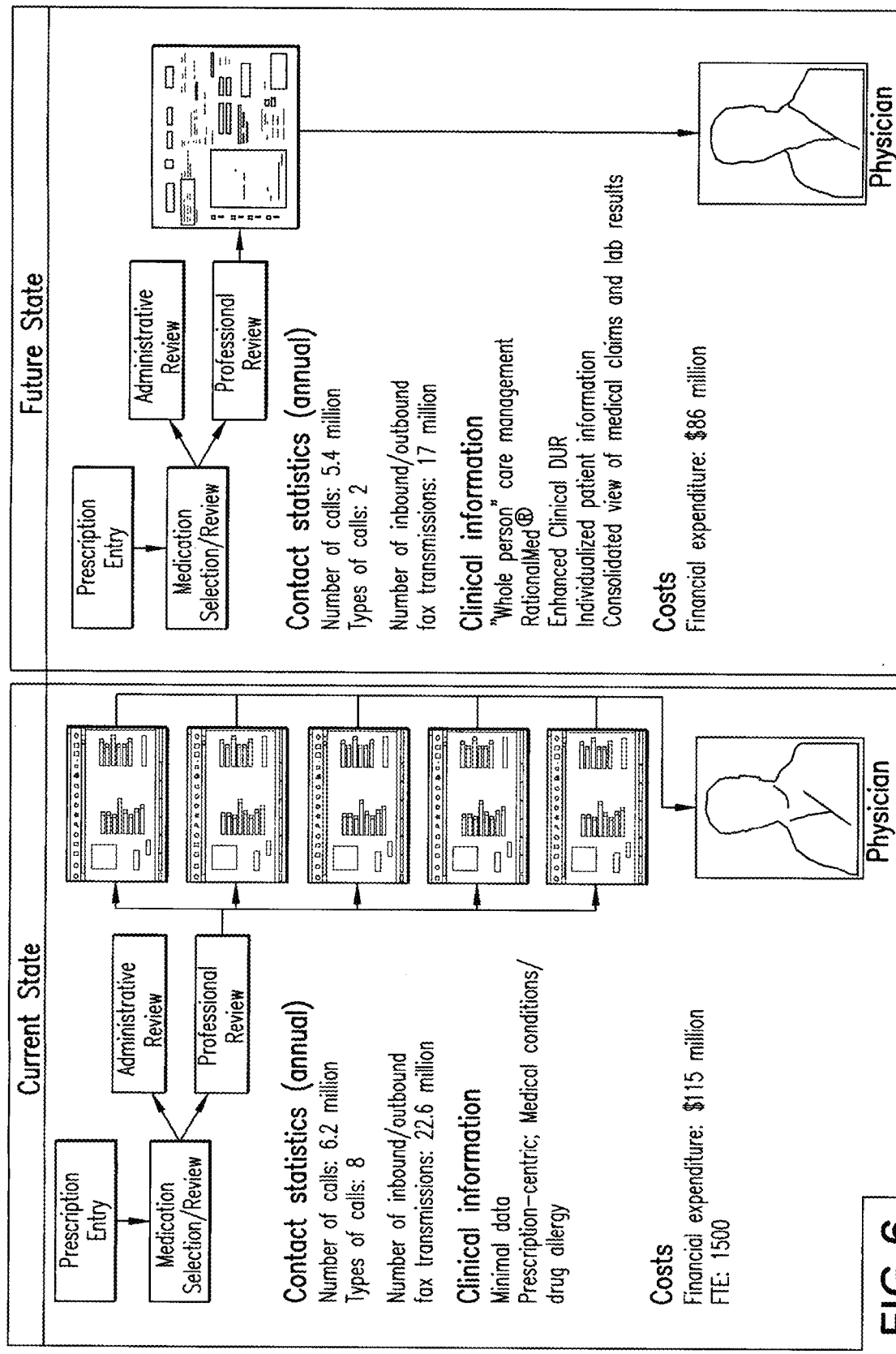
FIG. 6 illustrates work routed to individual therapeutic pharmacies within a network of therapeutic pharmacies.
Figure 7:
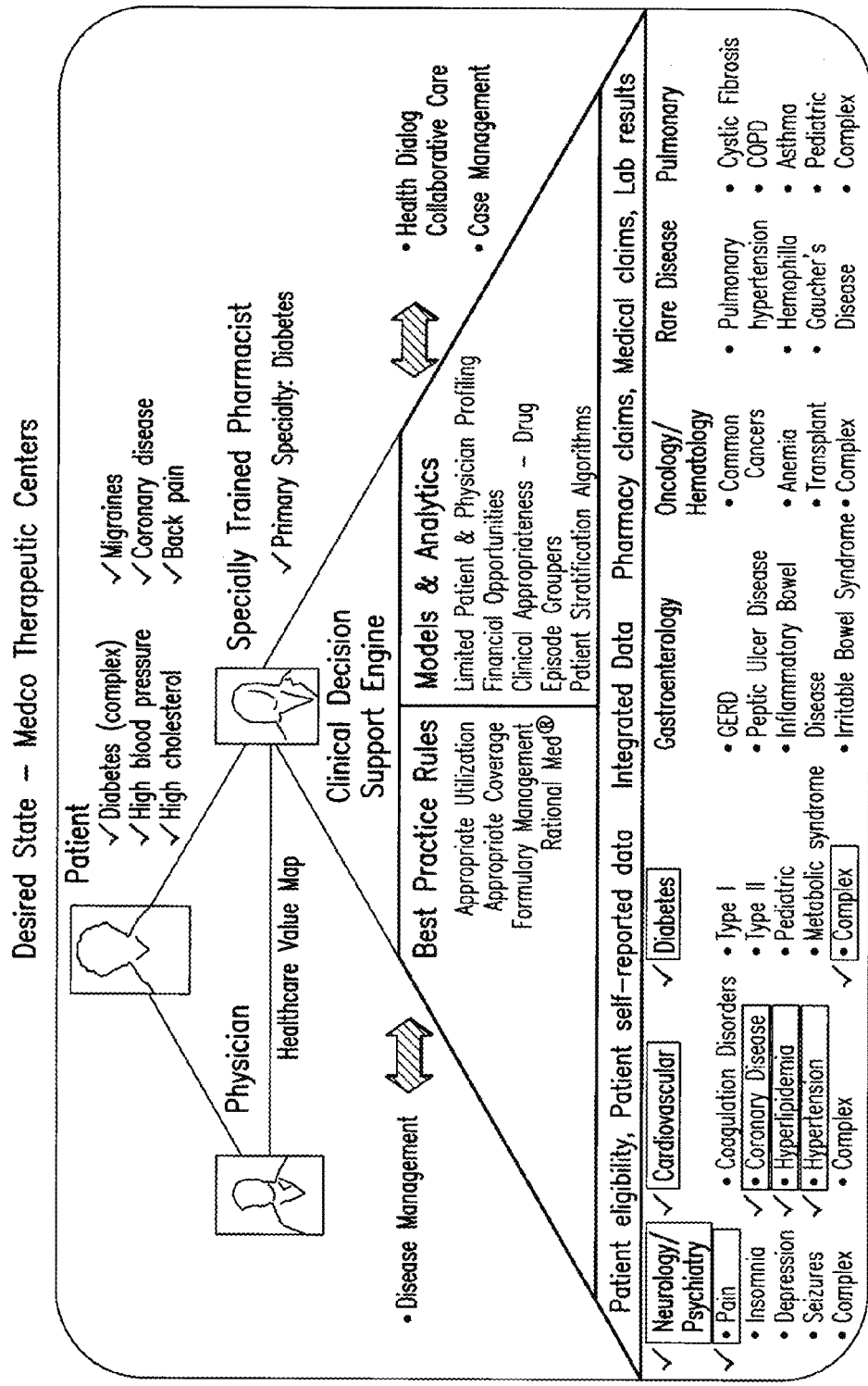
FIG. 7 illustrates the work load of a particular pharmacy within the network of pharmacies.

In assigning tasks, workers are entities that are capable of performing work. An additional component of each task assignment is a time constraint, which is some limitation on when the work must be performed—generally a deadline, but might include additional restrictions, such as "only call Dr. Lerner between 3 pm and 5 pm". A schedule is the collection of all pending (created but not resolved) tasks. The scope of a schedule might be a single worker, groups of workers, or even the universal schedule (all workers at all pharmacies). A schedule is conforming if it complies with client and regulatory constraints. A task represents a particular instantiation of a general process. It is explicitly represented by a process definition, which specifies, among other things, the steps in a process (i.e., subprocesses), required resources, required participants (e.g., pharmacist, prescriber), and definitions of process state, namely preconditions, run-constraints, and post conditions, which specify, respectively, what will be true before, during, and after a process is executed. A state is represented by a set of facts (conditions) that hold in that state of the world. An analogy can be made to functions in a software language, where there is a single definition of the function expressed in terms of abstract parameters, then multiple actual instantiations (i.e., function calls) where the parameters are replaced by actual, specific instances. In this context, protocols will be the level of process we are concerned with, tasks will be specific instances of protocols, dealing with a particular work order, assigned to particular workers (e.g., pharmacists). This architecture can handle tasks assigned to machines, software applications, or human workers, though the focus here is on tasks that will be handled by a person. Both tasks and workers can represent single entities, or collections of entities, or collections of other collections. On the task side, the most primitive, indivisible unit of work is called a Work Item. Generally, a work item will be to attempt to resolve a single alert by following its specified protocol. A task that is composed of other tasks is called a 'composite task', or 'work bundle'. There are many possible flavors of work bundle, depending on what the subtasks of a bundle have in common. For example, a 'contact bundle' is a collection of tasks that can be performed during a single contact with a prescriber. An 'order bundle' is the collection of all tasks for a single order. Essentially, a bundle is a collection of tasks that can be treated as if it were a single, atomic work item. OWL comprises primary components of a controller, an estimator, monitors, seeker, and an optimizer. The controller is the central manager, orchestrating the use of the other components. Monitors receive event notifications from the rest of the system (e.g., work completed, worker calls in sick, etc.) and provide this information to the other scheduling components, such as "how many tasks are currently pending throughout all pharmacies and how does that differ from X minutes ago." The estimator is the ultimate judge as to which schedule is best, by computing estimates of how long it will take to complete a schedule, how many resources will be required, and the value of completing the work (costs and benefits), ultimately producing a utility score, in dollars, that represents the total value of a candidate schedule. The optimizer module is responsible for implementing an optimization strategy that utilizes the seeker component to generate new candidate schedules and the estimator to decide which candidate is best. The role of seeker is to make recommendations to the optimizer on how to assign new work and to propose changes to existing schedules. The overall process will roughly go as follows. There will always be the currently executing schedule, managed by the controller, consisting of the universe of all work bins, each containing the set of tasks assigned to that bin. Simultaneously, the optimizer will be carrying out a particular, configurable optimization strategy, attempting to construct new schedules that are better than, and will eventually replace, the current schedule. Periodically, the optimizer will notify the controller that it has created a superior schedule, at which point, if the controller accepts the new schedule, work items (tasks) will be placed or moved to implement the task assignments of the new schedule. The workflow component is not responsible for making decisions on who, when, or what work to do. Instead, the workflow component is responsible for carrying out the managing of that work. The workflow component will receive a message with the following three pieces of data: a) work that needs to be performed; b) who is assigned to perform that work; and c) when the work should be carried out. Upon receipt, the workflow component will associate the given work with the given user, manage the work (for example carry out the schedule and authorization of work), and provide Enterprise Application Integration (EAI) capabilities as defined in a configurable business process model (i.e., execution plan). When associating work with the user, the workflow component will take as input the work item and associate it with the provided user. Once the user is associated with the work item, the workflow component is responsible for ensuring the necessary security mechanisms are enforced so that only the associate user can acquire, view, update, delete, and reassign the work. Managing the work includes all of the basic authorization issues related to ensuring only the authorized user can access the associated work item. Managing the work also extends to idea of carrying out a schedule; meaning that if the authorized user does not resolve the work in a particular amount of time, the workflow component will send a message back to one of OWLb's services indicating that the work is not yet resolved. This OWLb service will then determine the same three identifiers as before (what, who, when) and instruct the workflow component to manage the updated work. OWLb will read this plan in order to orchestrate the communication between its optimizer and seekers. This will provide a configurable means to define how the schedule will be improved upon. For example, the schedule may be flowed from one seeker to the next, allowing each to improve upon the previous schedule and the optimizer just selects the last schedule. An alternative plan would be such that each seeker returns a single-schedule and the optimizer selects the best. In either case, the workflow engine will provide a configurable plan to allow such orchestrations of services. FIG. 6 illustrates the work routed according to the invention, wherein the numbers below the bars represent the number of prescriptions routed to particular pharmacies. FIG. 7 illustrates the workload at a particular pharmacy segmented into various disease categories as well as a chart of clinical score opportunities.

Therapeutic Pharmacy (800)

The network of therapeutic pharmacies of the invention may contain a plurality of individual therapeutic pharmacies, wherein the individual pharmacies are established to fill and dispense medications based on one or more wellness categories or diseases. Generally, there may be individual pharmacies for each of neurology/psychiatry, pulmonary, cardiovascular, diabetes, gastroenterology, oncology/hematology, rare diseases, etc. FIG. 4 illustrates two (2) such individual pharmacies within a network of comprising a plurality of individual pharmacies. Depending upon the classification of the patient into one or more categories, OWLb will route the prescription to the specific pharmacy within the network established to handle the prescription. The individual pharmacies will generally stock all of the medications associated with particular diseases. After the prescription is filled, it may be forwarded to the patient by any one of numerous conventional means, e.g., mail delivery, courier delivery, customer pick-up, etc. The establishment of individual therapeutic pharmacies within a network of pharmacies will provide improved efficiency in resolving protocol, discussing specific issues with prescription writers and patients, and filling and dispensing medications.

Therapeutic Pharmacist (900)

Within each individual pharmacy of the network of therapeutic pharmacies will be a plurality of pharmacist specifically trained to resolve protocol, discuss alternative medications with physicians and patients for the wellness state or disease classification of that individual pharmacy. A specially trained pharmacist, i.e., a pharmacist that sees similar prescriptions for similar diseases and wellness states on a regular basis will be more familiar with patient conditions and alternative medications within a particular class of medications of specific diseases than a pharmacist operating with a general pharmacy that provides medications for all possible disease categories.

Integrated Contact Management (ICM) (1000)

Figure 8:
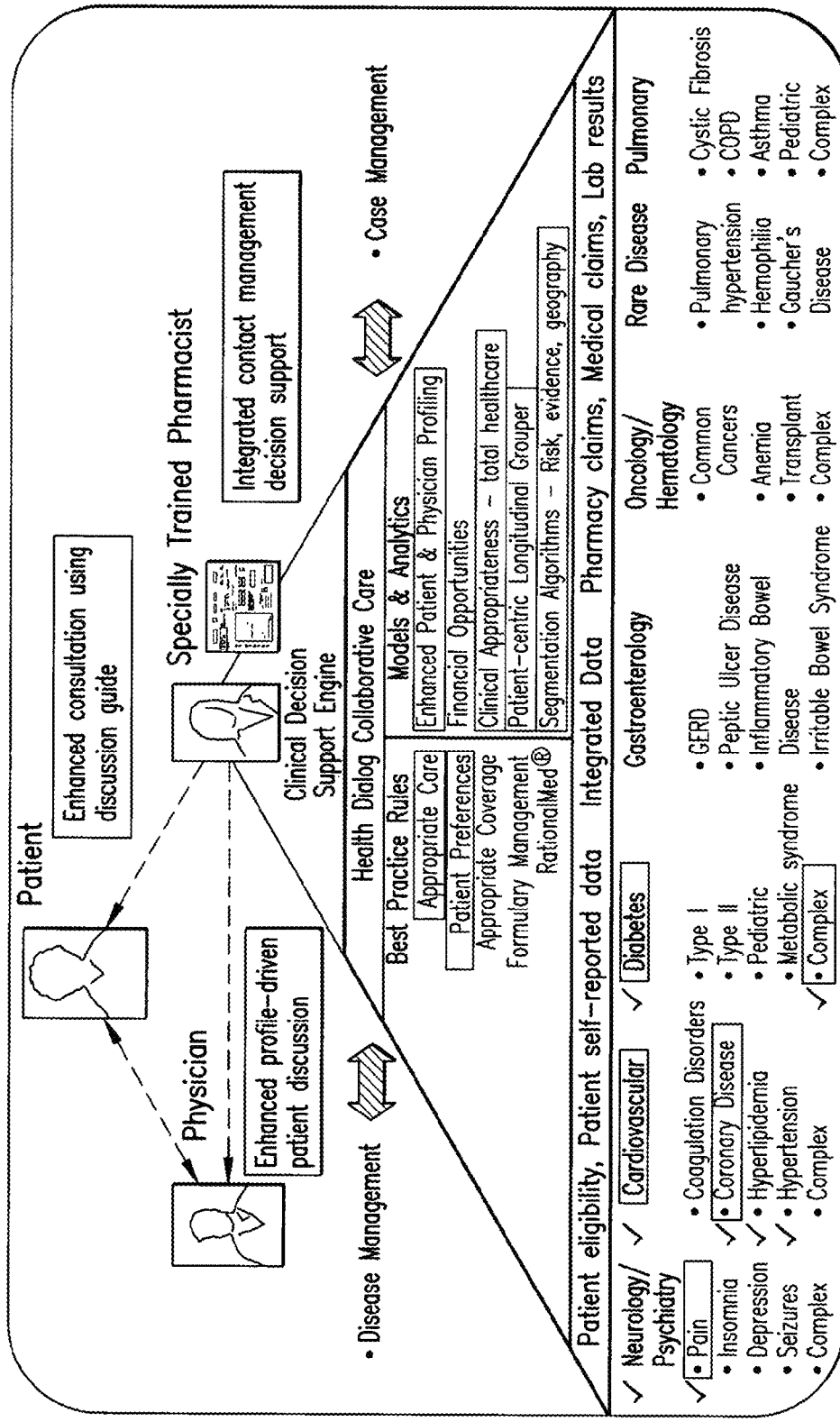
FIG. 8 is an illustration of a method of making clinical decisions of the present invention.
Figure 9:
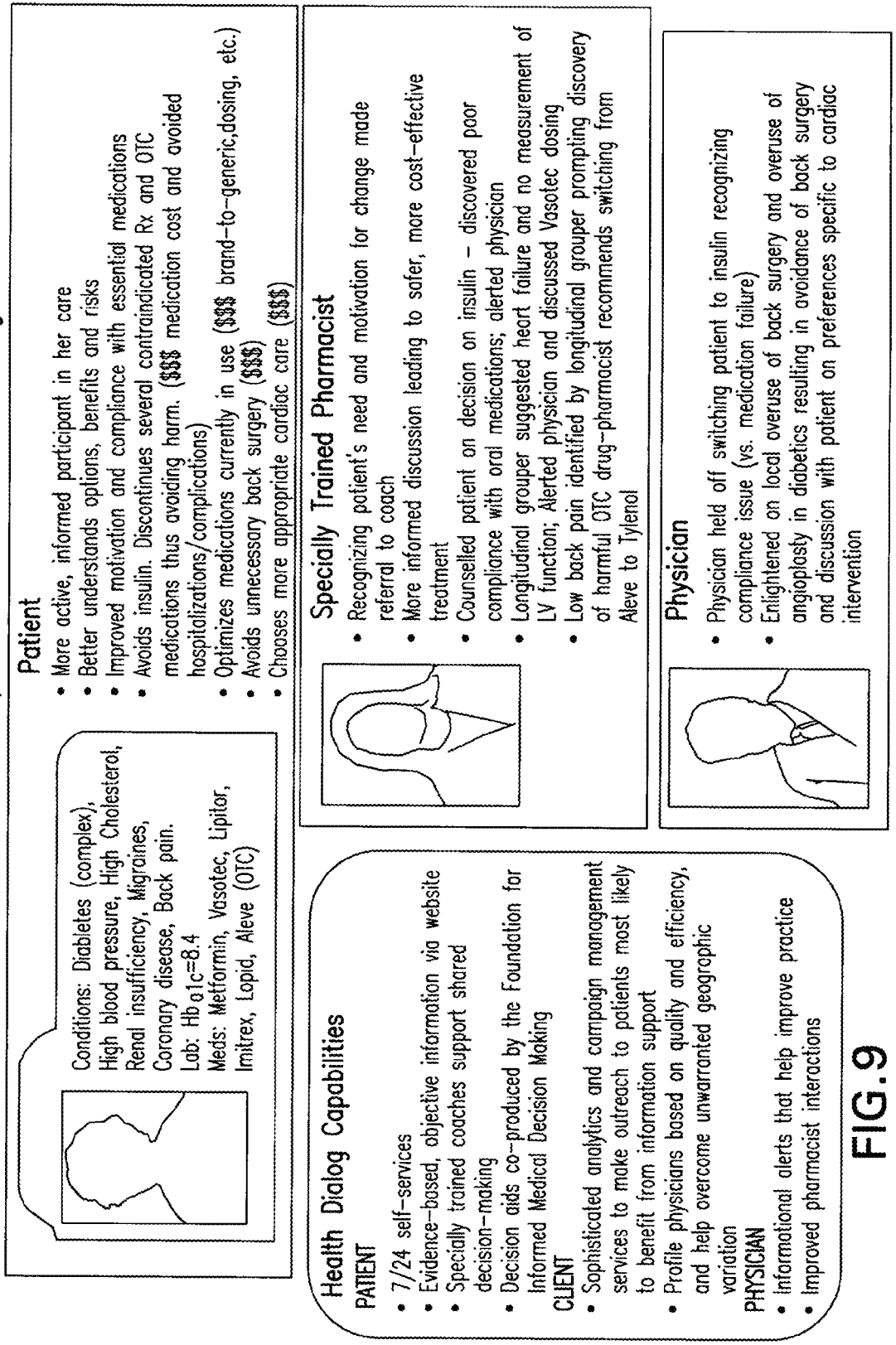
FIG. 9 is an illustration of a method of improving the dialog for making clinical decisions of the present invention.
Figure 10:
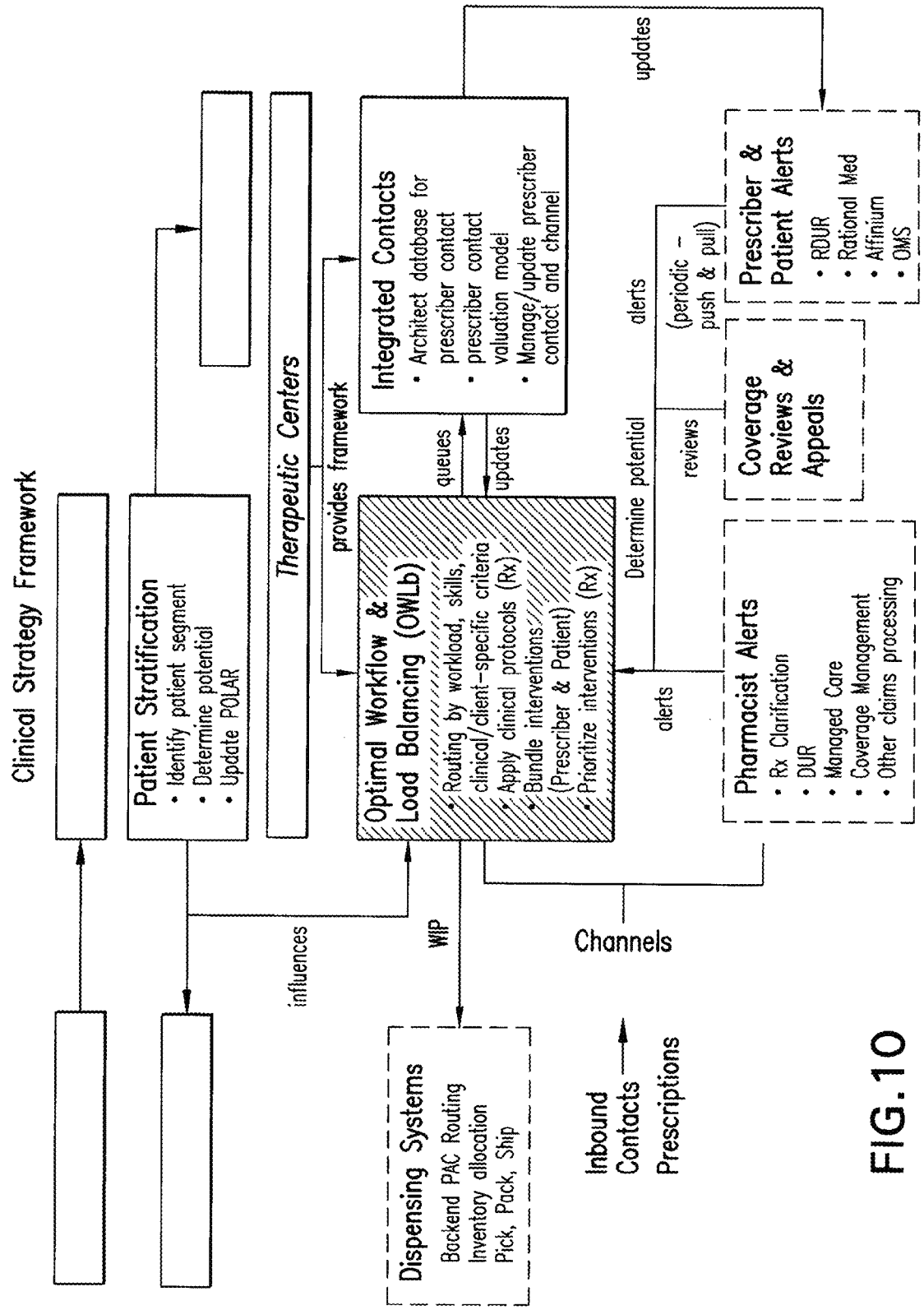
FIG. 10 is an illustration of a method of making clinical decisions of the present invention.
Figure 11:
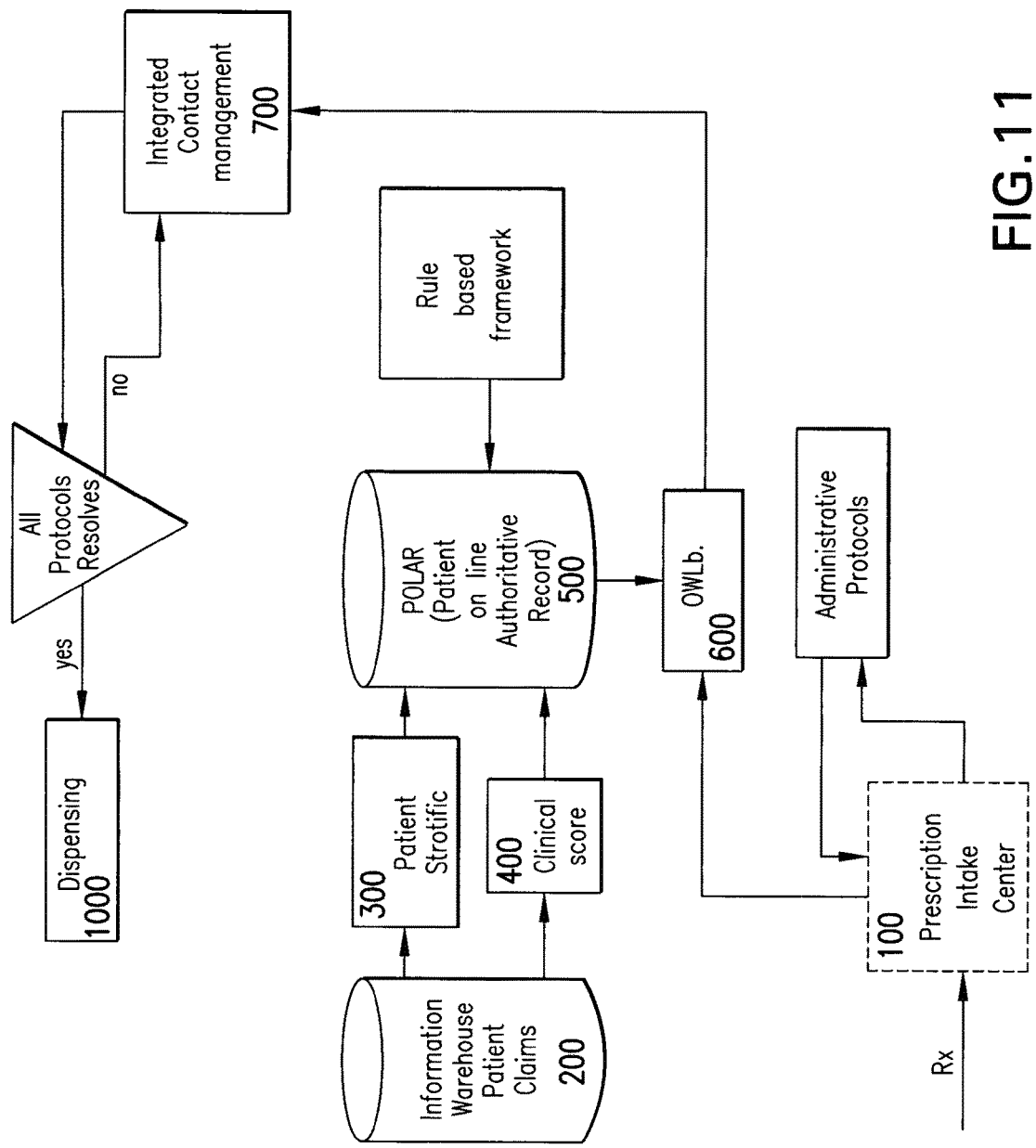
FIG. 11 is a diagram of a system suitable for practicing the clinical method of the present invention.
Figure 12:
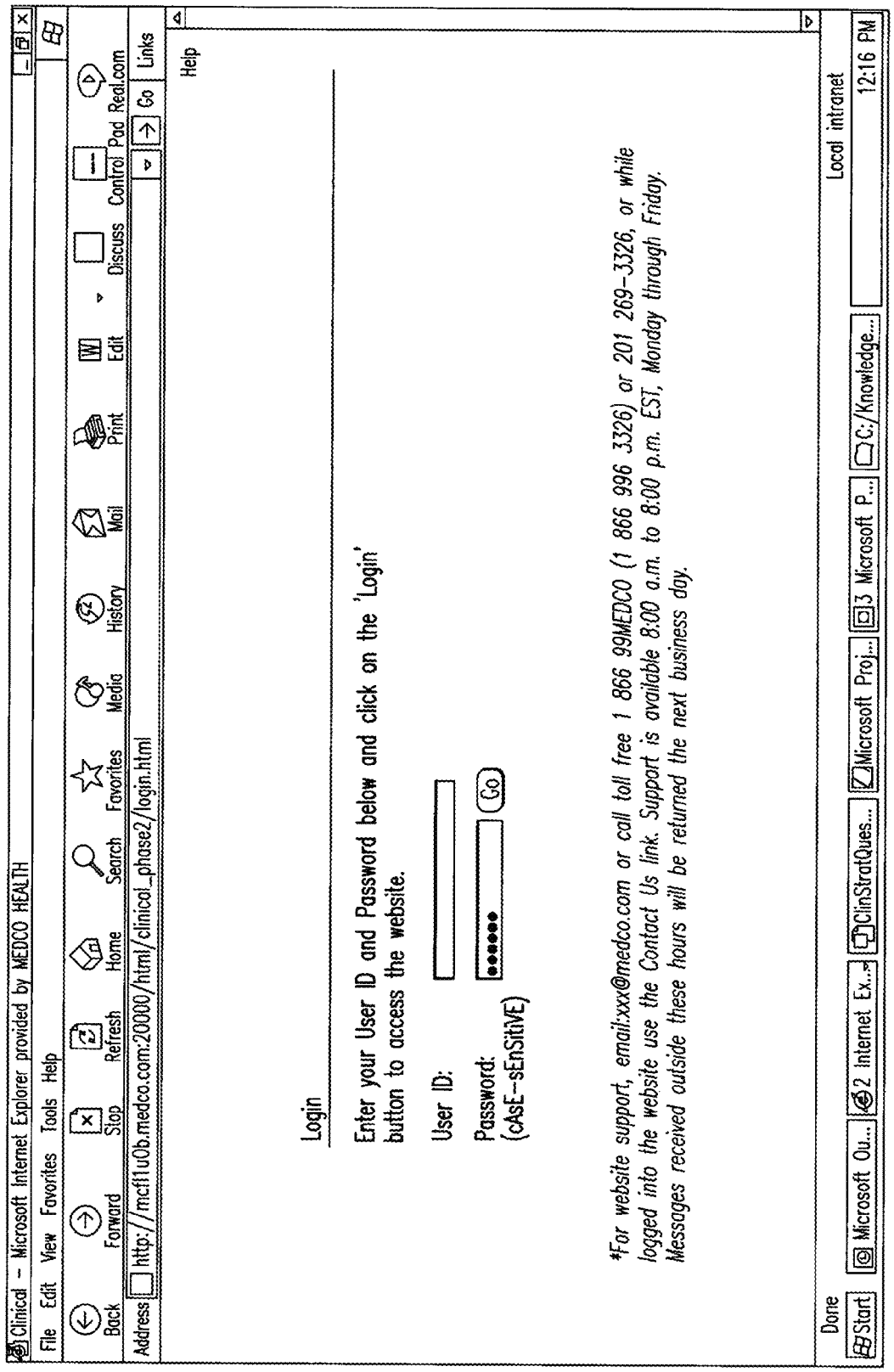
FIG. 12 is a screen shot of a system of the present invention wherein a login page is illustrated.
Figure 13:
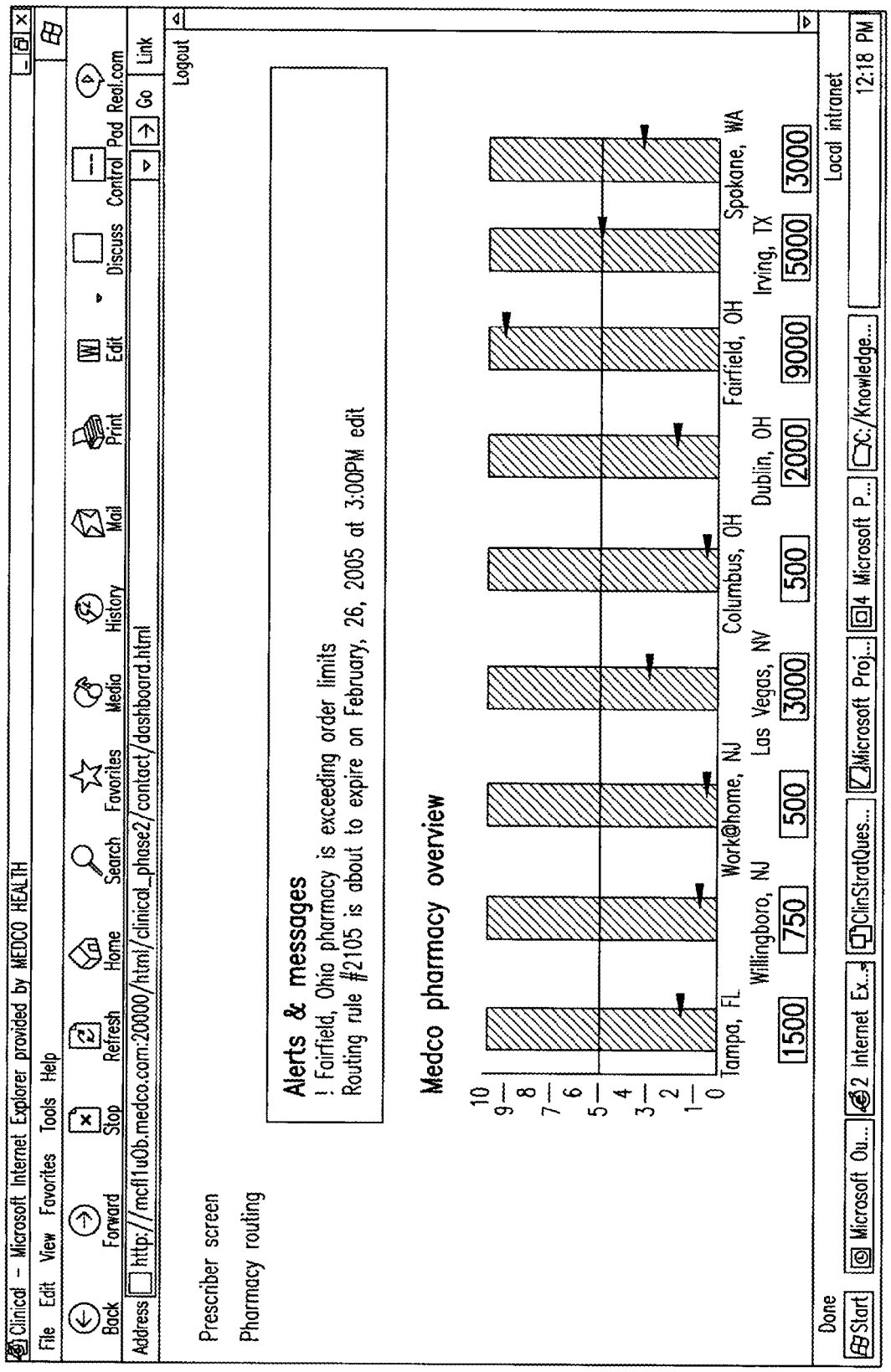
FIG. 13 is a screen shot of a system of the present invention wherein an alert of a system's pharmacy routing capacity chart is illustrated.
Figure 15:
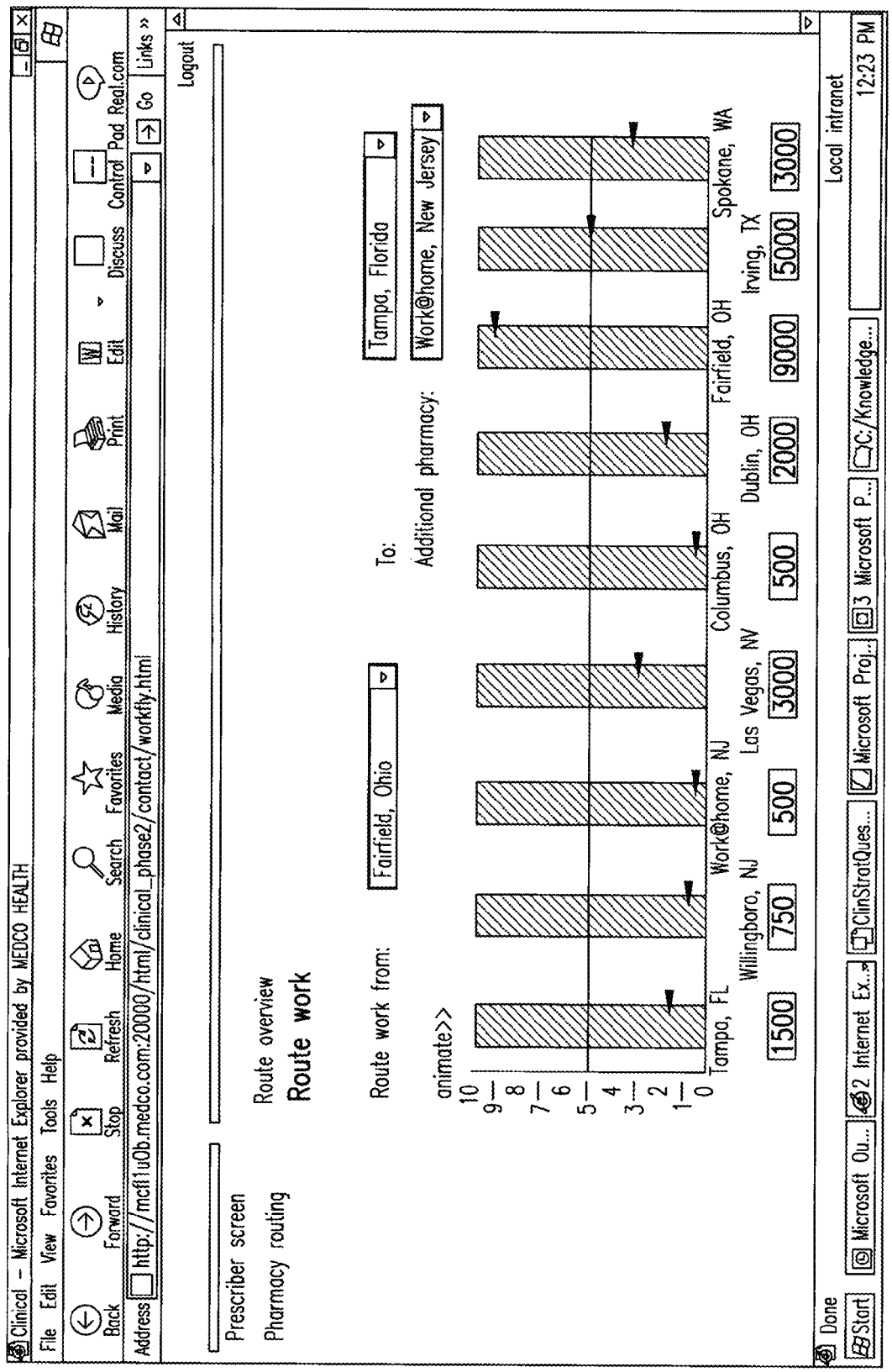
FIG. 15 is a screen shot of a system of the present invention wherein a routing capacity chart of a particular pharmacy is illustrated.
Figure 16:
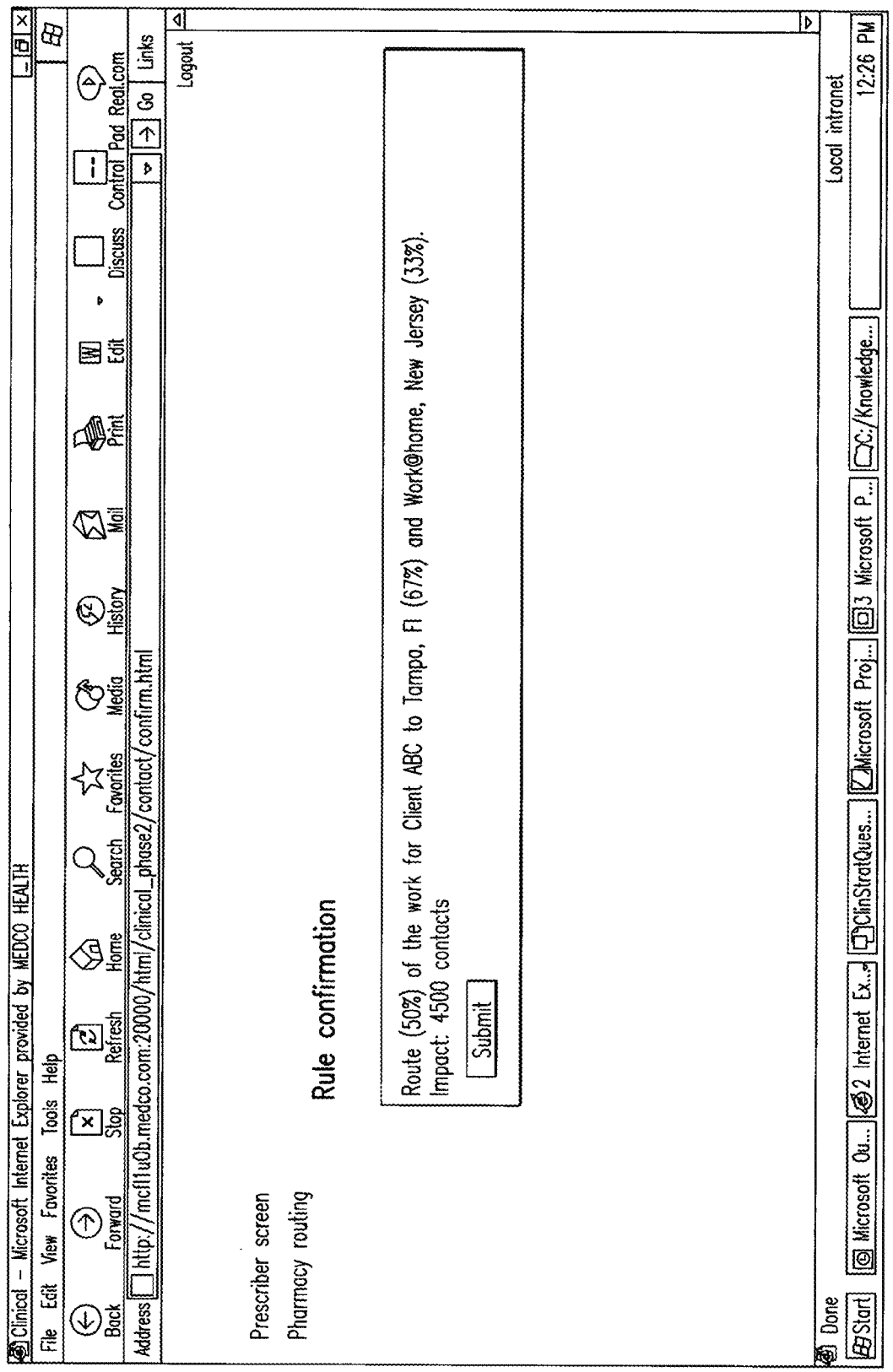
FIG. 16 is a screen shot of a system of the present invention wherein a pharmacy routing capacity rule confirmation may be requested.
Figure 18:
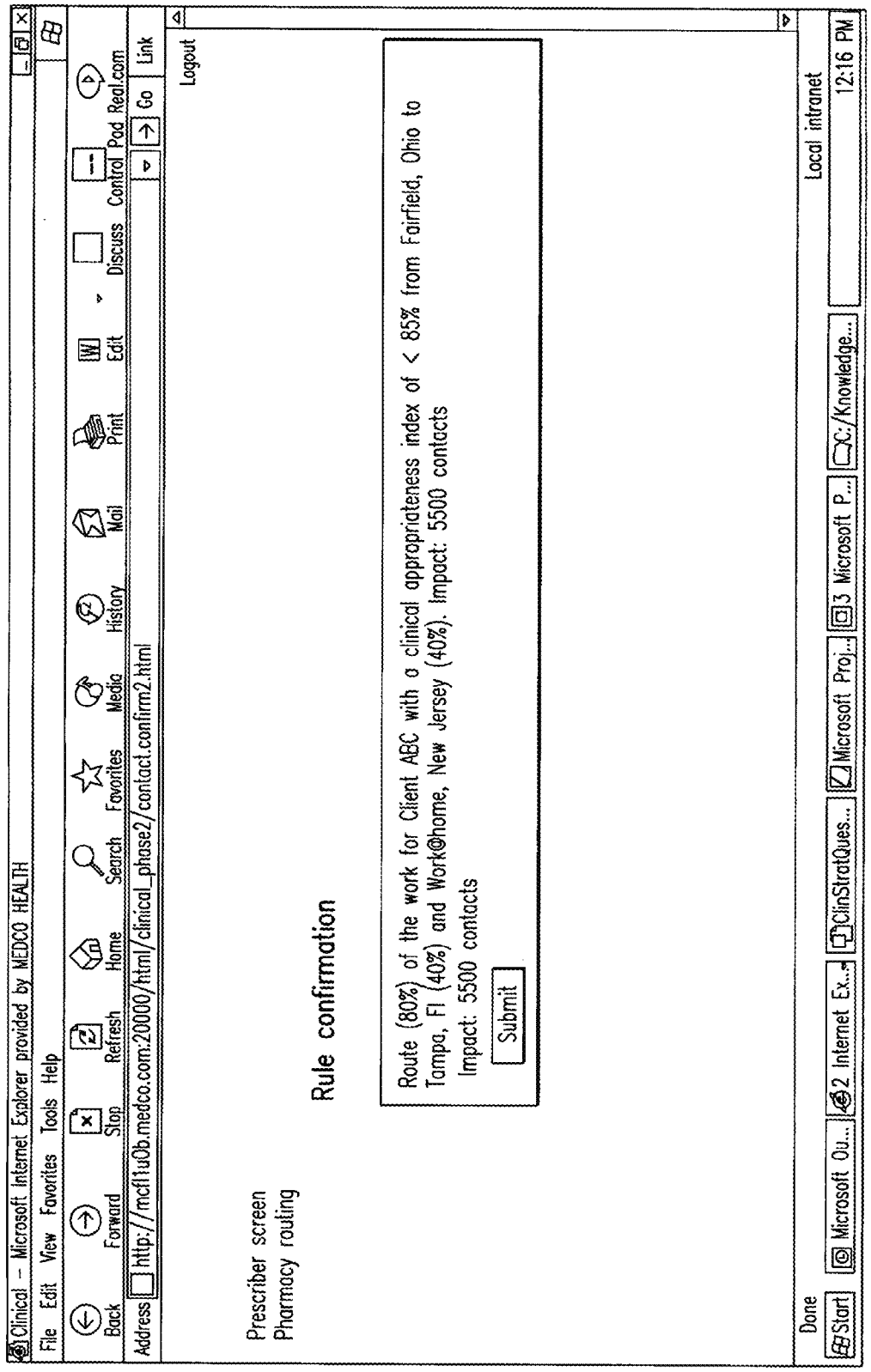
FIG. 18 is a screen shot of a system of the present invention wherein a rule confirmation for routing a prescription to a particular pharmacy is illustrated.

Integrated Contact Management (ICM) is responsible for providing a one-stop solution to our Pharmacists in resolving protocols associated with a patient's order. ICM receives work from OWLb as determined to be optimal for the current user of ICM. Upon receiving of the optimal work, Integrated Contact Management provides an integrated view of the patient information (stratification and clinical scoring), along with prescriber, client, and previous contact information to provide the end-user a complete picture of the patient and prescriber. The pharmacist establishes communication with the prescriber and uses ICM to resolve all open protocols and adjudicate the patient's order. OWLb may have also bundled many orders together, in which case the end user will attempt to adjudicate the remaining orders in the bundle while the prescriber is on the telephone. Essentially, ICM monitors and manages the time and work load of each individual therapeutic pharmacy as well as each pharmacist within the individual pharmacy. ICM is suitable for interfacing with physicians and health insurers to resolve any protocol issues with a prescription. ICM Summary Display is created and made available directly in the Alpha ICM screen in the Alpha Protocol Resolution application and the ICM Viewer application. A link to access mainframe Managed Care financial detail and processing screens is available directly in the Alpha ICM screen in the Alpha Protocol Resolution application and the ICM Viewer application. A patient detail display is available one click away from the ICM screen in the Alpha Protocol Resolution application and the ICM Viewer application. Member Detail Display is Clinical Opportunity Detail. New protocols may be generated on all complex orders, one for financial opportunities, one for clinical opportunities, and protocol resolution is used to track opportunity outcomes and metrics. FIGS. 8 and 9 illustrates a typical system print for a patient's unresolved protocols, wherein medications and correspondences, received and targeted delivery dates are shown.

We claim:

1. A method comprising:
   receiving a pharmaceutical prescription associated with a patient;
   accessing, on a processor, a medical record and a plurality of prescription claims for the patient;
   analyzing, on the processor, the medical record and the plurality of prescription claims to stratify the patient into a wellness category, the wellness category being based on a disease state, the disease state being based on a medical category;
   analyzing, on the processor, at least some of the plurality of prescription claims of the patient to determine a number of unique drugs obtained by the patient, to identify concurrent drug utilization review (CDUR) alert protocols that have a specific resolution code, to identify listed therapy optimization and omission of therapy rules that have triggered an alert, and to determine whether the patient is late with prescription refilling;
   generating, on the processor, a patient clinical score based on the a determination of the number of unique drugs obtained by the patient, an identification of the CDUR alert protocols that have a specific resolution code, an identification of the listed therapy optimization and omission of therapy rules that have triggered an alert, a determination that the patient is late with prescription refilling, the medical record, formulary information, and patient health insurance information; and
   routing, on the processor, the pharmaceutical prescription to a therapeutic pharmacy among a network of therapeutic pharmacies based on the wellness category and the patient clinical score, each therapeutic pharmacy within the network of therapeutic pharmacies being established in accordance with a particular wellness category.

2. The method according to claim 1, wherein the network of therapeutic pharmacies includes individual pharmacies for neurology, psychiatry, pulmonary, cardiovascular, diabetes, gastroenterology, oncology, hematology, rare diseases, and combinations thereof.

3. The method according to claim 1, wherein the wellness categories include a well category, an acute category, a chronic category, and a complex category.

4. The method of claim 1, further comprising:
filling and dispensing the pharmaceutical prescription at the therapeutic pharmacy.

5. The method of claim 1, further comprising:
assigning the pharmaceutical prescription to a pharmacist among a plurality of pharmacists in the therapeutic pharmacy based on skill and ability of the pharmacist.

6. The method of claim 5, wherein assignment of the pharmaceutical prescription is based on the skill and ability of the pharmacist and load balancing, the load balancing being based on current work load, schedule, and productivity rate of the plurality of pharmacists.

7. The method of claim 1, wherein the pharmaceutical prescription is received at a pharmacy intake center and the plurality of prescription claims are accessed from an information warehouse.

8. The method of claim 1, wherein routing the pharmaceutical prescription to the therapeutic pharmacy is based on the wellness category, the patient clinical score, and load balancing, the load balancing being based on current work load, schedule, and productivity rate.

9. The method of claim 1, wherein the pharmaceutical prescription is received over a computer network.

10. The method of claim 1, wherein the therapeutic pharmacy is capable of filling the pharmaceutical prescription for the patient.

11. The method of claim 1, wherein the processor is deployed with a computing device, the computing device configured to resolve protocol and perform drug utilization review for the subsequent filling and dispensing prescriptions for one or more diseases.

12. The method of claim 1, wherein the therapeutic pharmacy is further established to dispense a plurality of prescription drugs associated with the wellness category, the pharmaceutical prescription being for a prescription drug among the plurality of prescription drugs.

13. The method of claim 1, wherein the patient clinical score reflects a relative level of compliance by the patient with a medication associated with the pharmaceutical prescription.

14. The method of claim 1, wherein the patient clinical score reflects a relative level of possibility for the patient to utilize a less costly medication than a medication associated with the pharmaceutical prescription.

15. The method of claim 1, wherein the medical record and the plurality of prescription claims are further analyzed to stratify the patient into a disease category, and wherein the routing of the pharmaceutical prescription is based on the disease category, the wellness category, and the patient clinical score.

16. The method of claim 1, wherein the therapeutic pharmacy is capable of filling a prescription associated with the disease state.

17. The method of claim 1, wherein at least some of the plurality of prescription claims are the plurality of prescription claims associated with a certain period of time.

18. The method of claim 1, wherein routing comprises:
routing, on the processor, the pharmaceutical prescription to the therapeutic pharmacy among the network of therapeutic pharmacies based on a disease state associated with the patient, the wellness category, and the patient clinical score, each therapeutic pharmacy within the network of therapeutic pharmacies being established in accordance with a particular wellness category and a particular disease state, the therapeutic pharmacy to which the pharmaceutical prescription is routed having the disease state of the patient as the particular disease state.

19. A non-transitory machine-readable medium comprising instructions, which when executed by one or more processors, cause the one or more processors to perform the following operations:
receive a pharmaceutical prescription associated with a patient;
access a medical record and a plurality of prescription claims for the patient;
analyze the medical record and the plurality of prescription claims to stratify the patient into a wellness category, the wellness category being based on a disease state, the disease state being based on a medical category;
analyze at least some of the plurality of prescription claims of the patient to determine a number of unique drugs obtained by the patient, to identify concurrent drug utilization review (CDUR) alert protocols that have a specific resolution code, to identify listed therapy optimization and omission of therapy rules that have triggered an alert, and to determine whether the patient is late with prescription refilling;
generate a patient clinical score based on the a determination of the number of unique drugs obtained by the patient, an identification of the CDUR alert protocols that have a specific resolution code, an identification of the listed therapy optimization and omission of therapy rules that have triggered an alert, a determination that the patient is late with prescription refilling, the medical record, formulary information, and patient health insurance information; and
route the pharmaceutical prescription to a therapeutic pharmacy among a network of therapeutic pharmacies based on the wellness category and the patient clinical score, each therapeutic pharmacy within the network of therapeutic pharmacies being established in accordance with a particular wellness category.

* * * * *